(12) United States Patent
Hayashi et al.

(10) Patent No.: US 7,262,399 B2
(45) Date of Patent: Aug. 28, 2007

(54) AUTOMATIC EXPOSURE CONTROL METHOD OF IMAGE AND AUTOMATIC EXPOSURE CONTROL SYSTEM USING THE METHOD

(75) Inventors: Takeshi Hayashi, Kyoto (JP); Kouichi Sonobe, Kyoto (JP); Takahiro Yoshimura, Kyoto (JP); Masakazu Suzuki, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 190 days.

(21) Appl. No.: 11/119,510

(22) Filed: Apr. 28, 2005

(65) Prior Publication Data

US 2005/0242269 A1    Nov. 3, 2005

(30) Foreign Application Priority Data

Apr. 30, 2004  (JP) .............................. 2004-136620

(51) Int. Cl.
  *H04N 3/14* (2006.01)
  *H05N 1/64* (2006.01)
(52) U.S. Cl. .............................. 250/208.1; 250/370.09; 378/98.8
(58) Field of Classification Search ............. 250/208.1, 250/370.09; 378/98, 98.5, 98.8
See application file for complete search history.

(56) References Cited

U.S. PATENT DOCUMENTS

| 5,331,682 A | * | 7/1994 | Hsieh ........................... 378/19 |
| 5,530,238 A | * | 6/1996 | Meulenbrugge et al. . 250/208.1 |
| 5,617,462 A | | 4/1997 | Spratt |
| 6,351,519 B1 | | 2/2002 | Bonk et al. |
| 2002/0085672 A1 | | 7/2002 | Ganin et al. |
| 2003/0002624 A1 | | 1/2003 | Rinaldi et al. |

FOREIGN PATENT DOCUMENTS

| DE | 19734717 | 2/1999 |
| JP | 62-43990 | 2/1987 |
| JP | 6-38950 | 2/1994 |
| JP | 2000-175907 | 6/2000 |
| JP | EP 1 337 107 | 8/2003 |

* cited by examiner

*Primary Examiner*—John R. Lee
(74) *Attorney, Agent, or Firm*—Koda & Androlia

(57) ABSTRACT

An automatic exposure control method for an image produced on a solid-state image sensing device in which intensity of radiation light irradiated to an object to be examined from a radiation source is feedback controlled. The solid-state image sensing device comprises a picture element producing part where electric charges generated by way of photo-electric conversion when receiving exposure, and a dark current measuring part where a dark current is generated and stored without receiving exposure. The image is produced while performing radiography in a manner that the intensity of radiation light is feedback controlled so as to keep, within a predetermined density range, the amount value which is defined by removing the charge signals stored on a specified pixel element or a specified pixel element column in the dark current measuring part of the image sensing device from the charge signals stored on a specified pixel element or a specified pixel element column in the picture element producing part of the image sensing device.

10 Claims, 20 Drawing Sheets

| position | output ratio |
|---|---|
| n | $\alpha(pn)$ |
| n−1 | $\alpha 2(pn-1)$ |
| ⋮ | ⋮ |
| g | $\alpha 2(pg)$ |
| ⋮ | ⋮ |
| 1 | $\alpha 2(p1)$ |
| 0 | 1 | picture element producing part: rows n down to 1
dark current measuring part: row 0

*Fig.3*

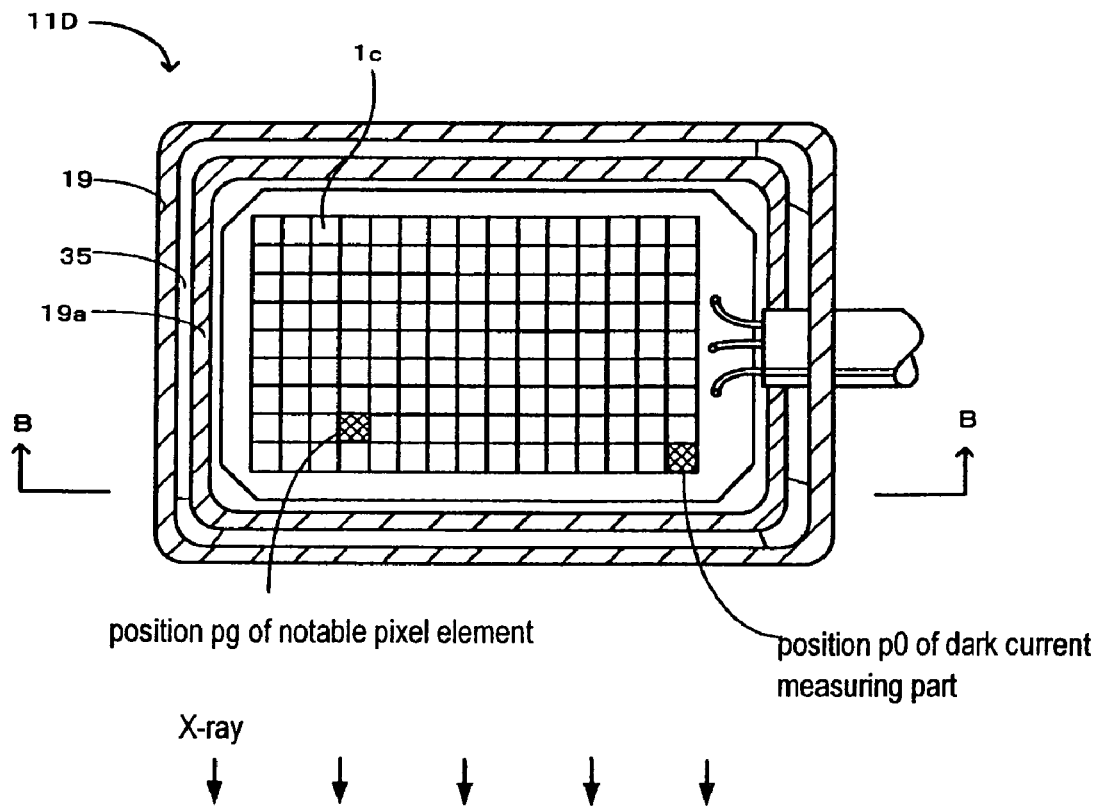

AUTOMATIC EXPOSURE CONTROL METHOD OF IMAGE AND AUTOMATIC EXPOSURE CONTROL SYSTEM USING THE METHOD

FIELD OF THE INVENTION

The present invention relates to an automatic exposure control method preferably applicable to imaging using a solid-state image sensing device and an automatic exposure control system using the automatic exposure control method. Here, the solid-state image sensing device includes one which exposes a visible light and one which exposes X-rays.

PRIOR ART

There are following prior arts disclosing an exposure control of an X-ray imaging apparatus.

JP-A-62-43990 discloses a radiography method in which a photoconductor for converting X-ray is charged with electricity before being exposed with X-rays or after scanning an image, the surface is scanned without exposing X-rays, and the image value of dark discharge image is subtracted from the image value of X-ray image.

Further JP-A-2000-175907 discloses a dark current compensation technology in case of a panoramic radiography with CCD sensor in which the signals of an exposure part of CCD sensor is compared with the signals of a dark current component of an unexposed part to execute compensation of a dark current compensation.

Still further, JP-A-6-38950 discloses an X-ray imaging apparatus in which a photodiode for monitoring a radiation dose is formed at the back of a base plate of a solid-state image sensing device such as CCD sensor and the X-ray output is controlled by detecting the transmitted X-rays with the photodiode in real time during radiography.

Still further Japanese Patent No. 3307519 discloses a medical X-ray imaging apparatus in which a dosage sensor for detecting the X-ray amount transmitted through an object is provided for an X-ray imaging device adjacent to CCD sensor. The X-ray amount entering in the CCD sensor is detected with the dosage sensor in advance and an X-ray generator is feedback controlled.

However, according to JP-A-62-43990, a particular X-ray imaging element such as a photoconductor for converting X-ray like selenium is required, so that there is a problem such that a high process speed with a high resolution like a solid-state image cannot be achieved and the apparatus costs much. Further according to this method, the image value of dark discharge image for all of the photoconductor for converting X-ray is introduced by charging the photoconductor with electricity before or after X-ray exposure and the introduced value is subtracted from the image value at the same image point of X-ray image to execute compensation. If the radiography conditions like a radiography time are different from that when the dark discharge image is obtained, appropriate compensation is not executed. Further, the prior art does not suggest feedback control of an X-ray generator.

According to JP-A-2000-175907, the dark current signals of an unexposed part of CCD sensor of a panoramic X-ray imaging apparatus are used for compensating the dark current. However, the dark current compensation is not executed at the same time of radiography, so that feedback control for an X-ray generator is not achieved. Automatic exposure control has to execute a real time control, so that a real time signal processing is not possible in the prior art.

Further according to JP-A-6-38950, the transmitted X-ray during radiography is detected in real time by the photodiode provided at the back of the board, so that response of the entire loop has to be very fast in order to stabilize the X-ray amount by feeding back detection signals to an X-ray source. It is physically very difficult and such an apparatus becomes expensive because of a special structure.

Still further according to Japanese Patent No. 3307519, the X-ray amount entering in CCD sensor is detected in advance and the X-ray generator is feedback controlled. However, the dark current component in the output of the CCD sensor is not considered. Therefore, in case of such control like changing the scanning speed during radiography, even when the dark current component in the output of the CCD sensor is changed accordingly, such change of dark current component is not thought. This structure is also special and it costs great deal.

SUMMARY OF THE INVENTION

The present invention is proposed in order to solve the above-mentioned problems. The object of the present invention is to provide an automatic exposure control method in which the intensity of radiation light is feedback controlled such that the image of which dark control component is removed is within a predetermined density range and to provide an automatic control system using the method.

According to the automatic exposure control method for an image produced on a solid-state image sensing device in which intensity of radiation light irradiated to an object to be examined from a radiation source for producing an image is feedback controlled, the solid-state image sensing device comprises a picture element producing part where electric charges generated by way of photo-electric conversion when receiving exposure are stored as charge signals, and a dark current measuring part where a dark current is stored as charge signals without receiving exposure, and the image is produced while performing radiography in a manner that the intensity of radiation light is feedback controlled so as to keep, within a predetermined density range, the amount value which is defined by removing the charge signals stored on a specified pixel element or a specified pixel element column in the dark current measuring part of the image sensing device from the charge signals stored on a specified pixel element or a specified pixel element column in the picture element producing part of the image sensing device.

The amount value of the stored charge signals for feedback control as mentioned above can be set by subtraction the amount of charge signals stored in and outputted from a dark current measuring part in the image sensing device from charge signals stored in and outputted from that of a specified pixel element or a specified pixel element column in a picture element producing part of the image sensing device.

According to the automatic exposure control method for an image produced on a solid-state image sensing device in which intensity of radiation light irradiated to an object to be examined from a radiation source for producing an image is feedback controlled, the solid-state image sensing device comprises a picture element producing part where electric charges generated by way of photo-electric conversion when receiving exposure are stored as charge signals, and a dark current measuring part where a dark current is stored as charge signals without receiving exposure, and the image is produced while performing radiography in a manner that the intensity of radiation light is feedback controlled so as to keep, within a predetermined density range, the amount value which is defined by removing the charge signals stored on a specified pixel element or a specified pixel element column in the dark current measuring part of the image sensing device from the charge signals stored on a specified pixel element or a specified pixel element column in the picture element producing part of the image sensing device.

According to the automatic exposure control method for an image of the present invention, the ratio data for a fixed exposure time of the output of charge signals stored on a specified pixel element or a specified pixel element column in said dark current measuring part and in said picture element producing part, are prepared in advance, and said dark current component is removed wile performing radiography by executing a predetermined arithmetic operation for the stored charge signals taken out of said picture element producing part, based on said dark current measured in said dark current measuring part and said output ratio data.

According to the automatic exposure control method for an image of the present invention, the ratio data for a fixed exposure time of the output of charge signals stored on a specified pixel element or a specified pixel element column in the dark current measuring part and in the picture element producing part, are prepared in advance, and the dark current component is removed wile performing radiography by executing a predetermined arithmetic operation for the stored charge signals taken out of the picture element producing part, based on the dark current measured in the dark current measuring part and the output ratio data.

The ratio data for a fixed exposure time of the output of charge signals stored on a specified pixel element or a specified pixel element column in the dark current measuring part and in the picture element producing part means the ratio of output intensity of the dark current component (dark current) in the stored charge signals outputted from the dark current measuring part and the dark current component in the stored charge signals outputted from each pixel element or each pixel element column in the picture element producing part when the charge storage time of the solid-state image sensing device is set to be a predetermined time.

According to the automatic exposure control method for an image of the present invention, the intensity of radiation light is feedback controlled by adding predetermined delay factor for a control target value.

According to the automatic exposure control method for an image of the present invention, the intensity of radiation light is feedback controlled by adding predetermined delay factor for a control target value.

In order to add delay elements, analog process by means of a low pass filter with a condenser and resistance may be used or a digital process may be used such that a time attenuation factor is weighed on a past value to add on a present value.

Further according to the automatic exposure control method for an image of the present invention, said solid-state image sensing device executes a panoramic radiography, a cephalometric radiography, a linear scan radiography, a dental radiography or CT radiography.

According to the automatic exposure control method for an image of the present invention, the intensity of radiation light is feedback controlled by adding predetermined delay factor for a control target value.

Still further according to the automatic exposure control method for an X-ray image produced on a solid-state image sensing device of a medical digital X-ray imaging apparatus in which the intensity of X-rays irradiated from an X-ray generator for radiography is feedback controlled, the solid-state image sensing device comprises a picture element producing part where electric charges generated by way of photo-electric conversion when receiving exposure are stored as charge signals, and a dark current measuring part where a dark current is stored as charge signals without receiving exposure, and said image is produced while performing radiography in a manner that the intensity of X-rays is feedback controlled so as to keep, within a predetermined density range, the amount value which is defined by removing the charge signals stored on a specified pixel element or a specified pixel element column in said dark current measuring part of said image sensing device from the charge signals stored on a specified pixel element or a specified pixel element column in said picture element producing part of said image sensing device.

According to the automatic exposure control method for an X-ray image produced on a solid-state image sensing device of a medical digital X-ray imaging apparatus in which the intensity of X-rays irradiated from an X-ray generator for radiography is feedback controlled, the solid-state image sensing device comprises a picture element producing part where electric charges generated by way of photo-electric conversion when receiving exposure are stored, and a dark current measuring part where a dark current is stored as charge signals without receiving exposure, and the image is produced while performing radiography in a manner that the intensity of X-rays is feedback controlled so as to keep, within a predetermined density range, the amount value which is defined by removing the charge signals stored on a specified pixel element or a specified pixel element column in the dark current measuring part of the image sensing device from the charge signals stored on a specified pixel element or a specified pixel element column in the picture element producing part of the image sensing device.

Here, the object of automatic exposure control is limited to a medical digital X-ray image apparatus.

According to the automatic exposure control method for an X-ray image of the present invention, the ratio data for a fixed exposure time between the inclination of the output charge signals stored on a specified pixel element or on a specified pixel element column in said dark current measuring part and the inclination of the output charge signals stored on a specified pixel element or on a specified pixel element column in said picture element producing part, are prepared in advance, and said image is produced while performing radiography in a manner that the intensity of X-rays is feedback controlled so as to keep, within a predetermined density range, the image removed a dark current component by executing a predetermined arithmetic operation based on said dark current component taken out of said dark current measuring part and said ratio data.

According to the automatic exposure control method for an X-ray image of the present invention, the ratio data for a fixed exposure time between the inclination of the change in the output charge signals stored on a specified pixel element or on a specified pixel element column in the dark current measuring part and the inclination of the output charge signals stored on a specified pixel element or on a specified pixel element column in the picture element producing part, are prepared in advance, and the image is produced while performing radiography in a manner that the intensity of X-rays is feedback controlled so as to keep, within a predetermined density range, the image removed a dark current component by executing a predetermined arithmetic operation based on the dark current component taken out of the dark current measuring part and the ratio data.

The inclination of output change of a specified pixel element or a specified pixel element column in the dark current measuring part for a predetermined exposure time means the inclination when the stored charge signals outputted from the specified pixel element or the specified pixel element column in the dark current measuring part are expressed with a direct function of the charge storage time (coefficient of dark current component for exposure time).

According to the automatic exposure control method for an X-ray image of the present invention, a feedback control of said intensity of X-rays is executed by controlling at least one of an X-ray scanning speed, an X-ray tube current and an X-ray tube voltage.

According to the automatic exposure control method for an X-ray image of the present invention, a feedback control of the intensity of X-rays is executed by controlling at least one of an X-ray scanning speed, an X-ray tube current and an X-ray tube voltage.

Further according to the present invention, the automatic exposure control system of a medical digital X-ray imaging apparatus in which the intensity of X-rays irradiated from an X-ray generator for radiography is feedback controlled comprises a solid-state image sensing device comprising a picture element producing part where electric charges generated by way of photo-electric conversion when receiving exposure are stored as charge signals, and a dark current measuring part where a dark current is stored as charge signals without receiving exposure, and a control means for producing said image on said solid-state image sensing device by feedback controlling the intensity of X-rays while performing radiography, so as to keep, within a predetermined range, the amount value which is defined by removing the charge signals stored on a specified pixel element or a specified pixel element column in said dark current measuring part of said image sensing device from the charge signals stored on a specified pixel element or a specified pixel element column in said picture element producing part of said image sensing device.

According to the present invention, the automatic exposure control system of a medical digital X-ray imaging apparatus in which the intensity of X-rays irradiated from an X-ray generator for radiography is feedback controlled comprises a solid-state image sensing device comprising a picture element producing part where electric charges generated by way of photo-electric conversion where receiving exposure are stored as charge signals, and a dark current measuring part where a dark current is stored as charge signals without receiving exposure, and a control means for producing the image on the solid-state image sensing device by feedback controlling the intensity of X-rays while performing radiography, so as to keep, within a predetermined range, the amount value which is defined by removing the charge signals stored on a specified pixel element or a specified pixel element column in the dark current measuring part of the image sensing device from the charge signals stored on a specified pixel element or a specified pixel element column in the picture element producing part of the image sensing device.

Namely, the apparatus has the solid-state image sensing device having the picture element producing part which receives X-rays, produces a visible light, executes photo-electric conversion and stores the electric charge and a dark current measuring part which stores a dark current component without receiving X-rays. The apparatus further has the control processing means for feedback controlling the X-ray intensity in such a manner that the image obtained by removing the dark current component extracted from the dark current measuring part from the stored charge signals of the specified pixel element or the specified pixel element column extracted from the picture element producing part has density within a predetermined range.

Further according to the present invention, the automatic exposure control system comprises a memory for storing in advance the ratio data for a fixed exposure time between the inclination of the change in the output charge signals stored on a specified pixel element or on a specified pixel element column in said dark current measuring part and the inclination of the change in the output charge signals stored on a specified pixel element or on a specified pixel element column in said picture element producing part; and a control means for feedback controlling the intensity of X-rays so as to keep, within a predetermined density, the image removed a dark current component by executing a predetermined arithmetic operation based on said dark current component taken out of said dark current measuring part and said ratio data.

According to the present invention, the automatic exposure control system comprises a memory for storing in advance the ratio data for a fixed exposure time between the inclination of the change in the output charge signals stored on a specified pixel element or on a specified pixel element column in the dark current measuring part and the inclination of the output charge signals stored on a specified pixel element or on a specified pixel element column in the picture element producing part; and a control means for feedback controlling the intensity of X-rays so as to keep, within a predetermined density, the image removed a dark current component by executing a predetermined arithmetic operation based on the dark current component taken out of the dark current measuring part and the ratio data.

Control processing means stores in advance the inclination of the output change of a specified pixel element or a specified pixel element column in the dark current measuring part for a specified exposure time based on the dark current component extracted from the picture element producing part in case of removing the dark current component, obtains the inclination ratio to a specified pixel element or a specified pixel element column in the picture element producing part for a predetermined exposure time, and executes feedback control of the X-ray intensity in such a manner that the image which is obtained by an arithmetic operation based on the inclination ratio and of which dark current component is removed has density within a predetermined range.

Still further according to the automatic exposure control method of the present invention, a feedback control of said intensity of X-rays is executed by controlling at least one of an X-ray scanning speed, an X-ray tube current, an X-ray tube voltage, and a gradation process.

According to the automatic exposure control method of the present invention, a feedback control of the intensity of X-rays is executed by controlling at least one of an X-ray scanning speed, an X-ray tube current, an X-ray tube voltage, and a gradation process.

EFFECT OF THE INVENTION

When the automatic exposure control method proposed in the present invention is applied to an image production apparatus for producing an image by irradiating a light including a visible light on an object to be examined from an irradiation source, the image is produced in a manner that the intensity of radiation light is feedback controlled so as to keep, in a predetermined density range, the amount value which is defined by removing the charge signals stored on a specified pixel element or a specified pixel element column in the dark current measuring part of the image sensing device from the charge signals stored on a specified pixel element or a specified pixel element column in the picture element producing part of the image sensing device, thereby enabling to produce a preferred pixel image data without dark current component.

Further according to the automatic exposure control method proposed in the present invention, the inclination ratio of the output change of the stored charge signals of a specified pixel element or a specified pixel element column in the picture element producing part for a predetermined exposure time and the output change of the stored charge signals of a pixel element or at least one pixel element column in the dark current measuring part is used for operation, thereby facilitating the compensation processing.

Still further according to the automatic exposure control method of the present invention, the intensity of radiation light is feedback controlled with a predetermined delay factor for a control target value, so that striping noise caused by feedback control is not seen on resulting image.

Further according to the automatic exposure control method of the present invention, an automatic exposure control can be executed in case of a panoramic radiography, a cephalometric radiography, a linear scan radiography, a dental radiography or CT radiography.

According to the automatic exposure control method of the present invention, the above-mentioned methods are applied to a medical digital X-ray imaging apparatus, so that the same effects mentioned above can be achieved.

According to the automatic exposure control method in which the object of feedback control is at least one of an X-ray scanning speed, an X-ray tube current and an X-ray tube voltage, a suitable control target can be selected depending on radiography conditions and an automatic exposure control for a desirable image quality can be executed by combining them.

According to the medical digital X-ray imaging apparatus of the present invention, the same effects as those of the above-mentioned methods can be achieved.

BRIEF DESCRIPTION OF THE DRAWINGS

FIG. 3 is a dark current compensation table.

FIG. 18 is a sectional view of a detector for radiography constituting the medical digital X-ray imaging apparatus of FIG. 15.

DETAILED DESCRIPTION OF THE INVENTION

The automatic exposure control method of radiography image and a practical medical digital X-ray imaging apparatus using the method are explained hereinafter.

EMBODIMENT 1

Figure 1:
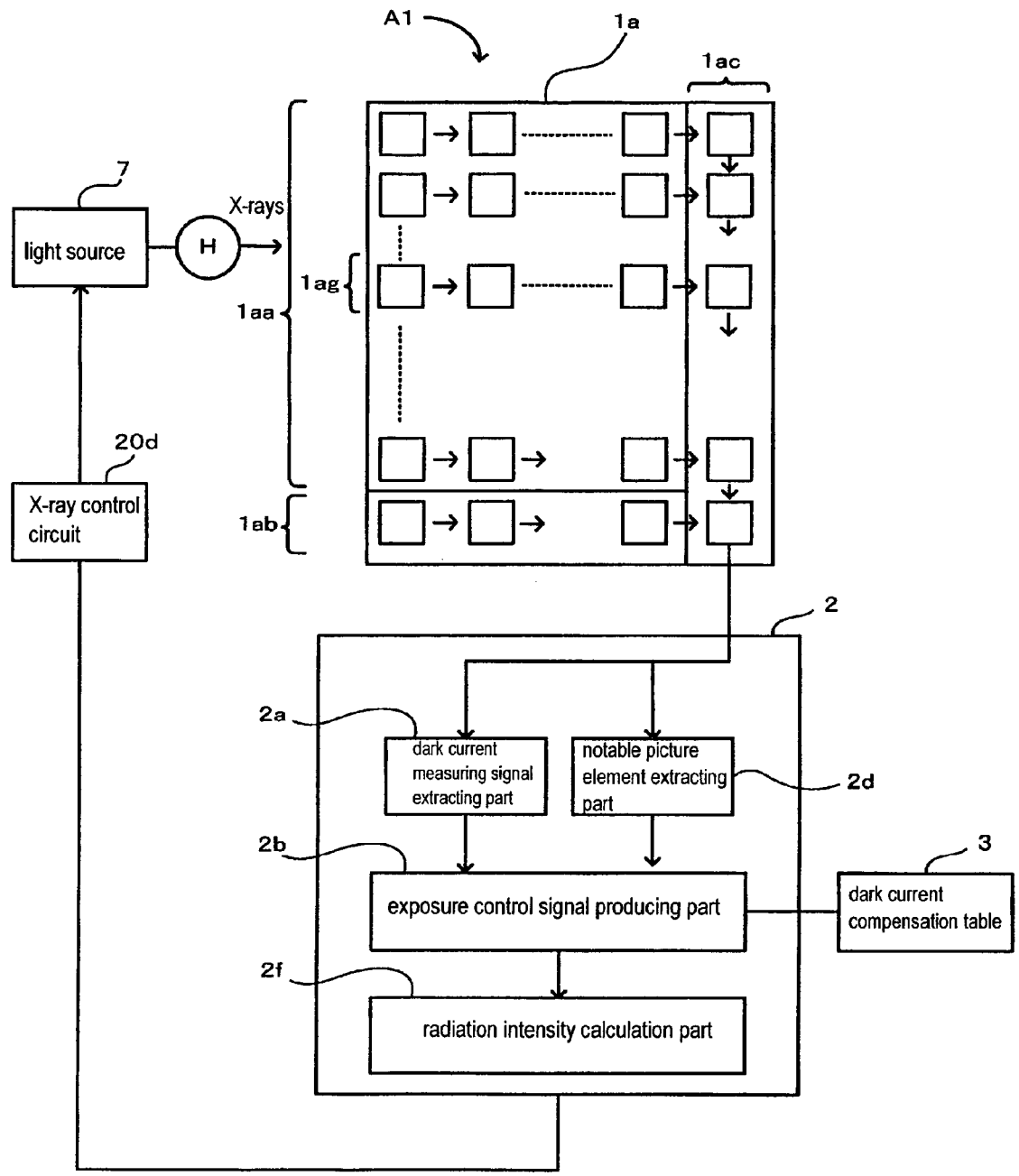
FIG. 1 is a block diagram of an automatic exposure control apparatus showing the concept of the present invention.

FIG. 1 explains the basic structure of the automatic exposure control apparatus of the present invention. The automatic exposure control apparatus A1 has a solid-state image sensing device 1a like CCD sensor which exposes the light irradiated from a radiation light source 7 and transmitted through an object H to be imaged, a control processing means 2, and a radiation source control means 20d. The solid-state image sensing device 1a is driven by a drive clock of an image sensing device drive circuit 1d which produces a drive clock from TDI (Time Delay Integration) clock and is divided into a picture element producing part 1aa, a dark current measuring part 1ab and a stored charge transferring part 1ac.

In the picture element producing part 1aa, CCD which charges and transfers the electric charge produced by light (X-rays and so on) with high energy is arranged in column. Also in the dark current measuring part 1ab, a single or plural columns of CCD like the picture element producing part 1aa are arranged. However, the CCD in the dark current measuring part 1ab is masked (shielding X-ray) so as not to always expose light. In the stored charge transferring part 1ac, CCD for transferring the electric charge outputted from each column in the picture element producing part 1aa and the dark current measuring part 1ab is arranged in column.

The stored charge signals from the picture element producing part 1aa and the dark current measuring signals from the dark current measuring part 1ab are sequentially outputted at a fixed timing from an outlet at the lower right into the control processing means 2.

A notable pixel element 1ag is set in the picture element producing part 1aa in order to execute automatic exposure control. The notable pixel element 1ag may be at an optional position in the picture element producing part 1aa, however, it may be preferably set in the interested area of the object to be imaged where the light receiving amount is not largely changed during radiography. In case of a dental panoramic radiography, it may be most preferably set a little above an upper jaw. The automatic exposure control of the present invention is executed based on the exposure measuring signals in which the dark current component is removed from the stored charge signals of the notable pixel element 1ag. The number of the notable pixel elements 1ag is not limited to one, but if there are more than two notable pixel elements 1ag, the average value thereof is used as exposure measuring signals.

The control processing means 2 removes the dark current component from the stored charge signals taken out of the picture element producing part 1aa during radiography. On the other hand, it feedback controls an X-ray radiation source control means 5. The control processing means 2 is comprised of an extracting part of dark current measuring signal 2a for extracting the dark current measuring signals from the stored charge signals outputted from a charge storage type image sensor 1 at a predetermined timing, a notable picture element extracting part 2d for extracting the stored charge signals of the notable pixel element at a predetermined timing, an exposure control signal producing part 2b for obtaining the exposure control signals in which the dark current component in the stored charge signals outputted from the notable pixel element 1ag is expected and calculated referring to parameters, which are described later, recorded in a dark current compensation table 3 per the stored charge signals outputted from the notable pixel element 1ag and based on the dark current measuring signals outputted from the dark current measuring part 1ab, and a radiation intensity calculating part 2f for outputting signals which calculates the radiation light intensity to be emitted from the radiography light source 4 based on the exposure control signals and outputs the signals for feedback controlling the radiation source control means 5.

The dark current compensation table 3 stores parameters in advance for expecting and calculating the dark current component caused when the electric charge in each column in the picture element producing part 1aa following a predetermined transfer channel, namely a crosswise transfer channel in each column and a vertical transfer channel in the stored charge transferring part 1ac, based on the dark current measuring signals (dark current component) measured in the dark current measuring part 1ab.

Here, the principle of automatic exposure control of exposure control apparatus is explained hereinafter.

Where the temperature at radiography is $\xi$, the electric charge accumulated in all the columns relative to each column (k=... 1, 0) in the picture element producing part 1aa and the dark current measuring part 1ab of the solid-state image sensing device 1a is transferred through the stored charge transferring part 1ac, and is outputted as stored charge signals Os(pk, $\xi$) and as the dark current measuring signals Os(P0, $\xi$), they are expressed by the following formula (I).

$$Os(pn, \xi) = Osx(pn, \xi) + Dk(pn, \xi) + Of(pn) \quad (I)$$
$$Os(pn-1, \xi) = Osx(pn-1, \xi) + Dk(pn-1, \xi) + Of(pn-1)$$
$$|$$
$$Os(p1, \xi) = Osx(p1, \xi) + Dk(p1, \xi) + Of(p1)$$
$$Os(p0, \xi) = Dk(p0, \xi) + Of(p0)$$

where
 Os: stored charge signal
 Osx: effective picture element signal based on exposure (signal component by the exposure of stored charge signal)
 Dk: dark current component of stored charge signal
 Of: offset component of stored charge signal
 p: position of column
 $\xi$: temperature On the other hand, when the solid-state image sensing device 1a is shielded so as not to expose, the stored charge signal Os(pk, $\xi$) and the dark current measuring signal Os(p0, $\xi$) are shown in the following formula (II) in the same manner.

$$Os(pn, \xi) = Dk(pn, \xi) + Of(pn) \quad (II)$$
$$Os(pn-1, \xi) = Dk(pn-1, \xi) + Of(pn-1)$$
$$|$$
$$Os(p1, \xi) = Dk(p1, \xi) + Of(p1)$$
$$= Dk(P0, \xi) + Of(p0)$$

It is known that the dark current component is substantially in ratio to the charge storage time T of the solid-state image sensing device 1a, so that the dark current component at the $k^{th}$ column is obtained by the following formula (III).

$$Dk(pk, \xi) = \alpha(pk, \xi) \cdot T \quad (III)$$

where
 $\alpha$: coefficient
 T: storage time

When the charge storage time T is varied in several ways, the stored charge signal Os(pk, $\xi$) and the dark current measuring signal Os(p0, $\xi$) are measured, and the least square method is applied, these direct functions may be suitable. However, in a simple method, those signals are measured for two charge storage times T and a straight line passing the two points can be determined.

Further, the output ratio $\alpha 2$ of the dark current component Dk(pk, $\xi$) at the $k^{th}$ column in the picture element producing part 1aa and the dark current component Dk(p0, $\xi$) of the dark current measuring part 1ab for a predetermined storage time T is obtained, it is an inclination ratio of the graph of the stored charge signal Os(pk, $\xi$) and the graph of the dark current measuring signal Os(p0, $\xi$) as follows.

$$\alpha 2(pk, \xi) = Dk(pk, \xi) / Dk(p0, \xi)$$
$$= \{\alpha(pk, \xi) \cdot T\} / \{\alpha(p0, \xi) \cdot T\}$$
$$= \alpha(pk, \xi) / \alpha(p0, \xi)$$

Wherein, the output ratio α (pk, ξ) is supposed to be divided into the part which depends on the place pk and the temperature ξ, $$\alpha(pk, \xi) = \alpha1(pk) \cdot \alpha2(\xi)$$

Accordingly, the output ratio α2 does not depend on the temperature ξ and becomes the following formula (IV).

$$\alpha2(pk) = \alpha1(pk)/\alpha1(p0) \tag{IV}$$

According to the formulas (I) and (IV), the effective picture element signal Osx(pk, ξ) based on the exposure of each column (k=n . . . 1) in the picture element producing part 1aa is expressed as follows by means of the dark current measuring signal Os(p0, ξ) when the temperature is ξ during radiography.

$$\begin{aligned} Osx(pk, \xi) &= Os(pk, \xi) - Dk(pk, \xi) - Of(pk) \\ &= Os(pk, \xi) - \alpha2(pk) \cdot Dk(p0, \xi) - Of(pk) \\ &= Os(pk, \xi) - \alpha2(pk) \cdot \\ &\quad \{Os(p0, \xi) - Of(p0)\} - Of(pk) \end{aligned} \tag{V}$$

As understood from the formula (V), when the stored charge signal Os(pg, ξ) of notable pixel element 1ag is compensated during radiography by means of the dark current measuring signal Os(p0, ξ) of the dark current measuring part 1ab according to the formula (V), the exposure measuring signals can be obtained in which the dark current component is removed.

Namely, according to the present invention, the notable picture element extracting part 2d extracts the exposure measuring signals Os(pg, ξ) from the stored charge signals outputted from the notable pixel element 1ag at a predetermined timing and the exposure control signal producing part 2b calculates the exposure control signals X according to the following formula.

$$X = Os(pg, \xi) - \alpha2(pg) \cdot Os(p0, \xi) \tag{VI}$$

where

X: exposure control signal pg: position of notable pixel element 1ag

Here, Of(pg) is removed from the formula (VI) because it is a constant number.

The radiation intensity calculating part 2f calculates the intensity of radiation light to be emitted according to the following formula and feedback controls the radiation source control means 5, thereby achieving an automatic exposure control.

$$I = -A \cdot X + B \tag{VII}$$

where

I: drive current of radiation light source to be generated in radiation source control means A, B: constant value In place of controlling the drive current of radiation light source, the drive voltage may be controlled in the same manner, both the drive current and the drive voltage may be controlled, or the scanning speed may be controlled in place of controlling the drive current. When the drive current or the scanning speed is controlled, the X-ray transmitted amount is changed as a whole and the brightness of the obtained X-ray image is changed. When the drive voltage is controlled, the energy distribution of transmitted X-ray is charged, so that the contrast of the obtained X-ray image is changed.

Figure 2A:
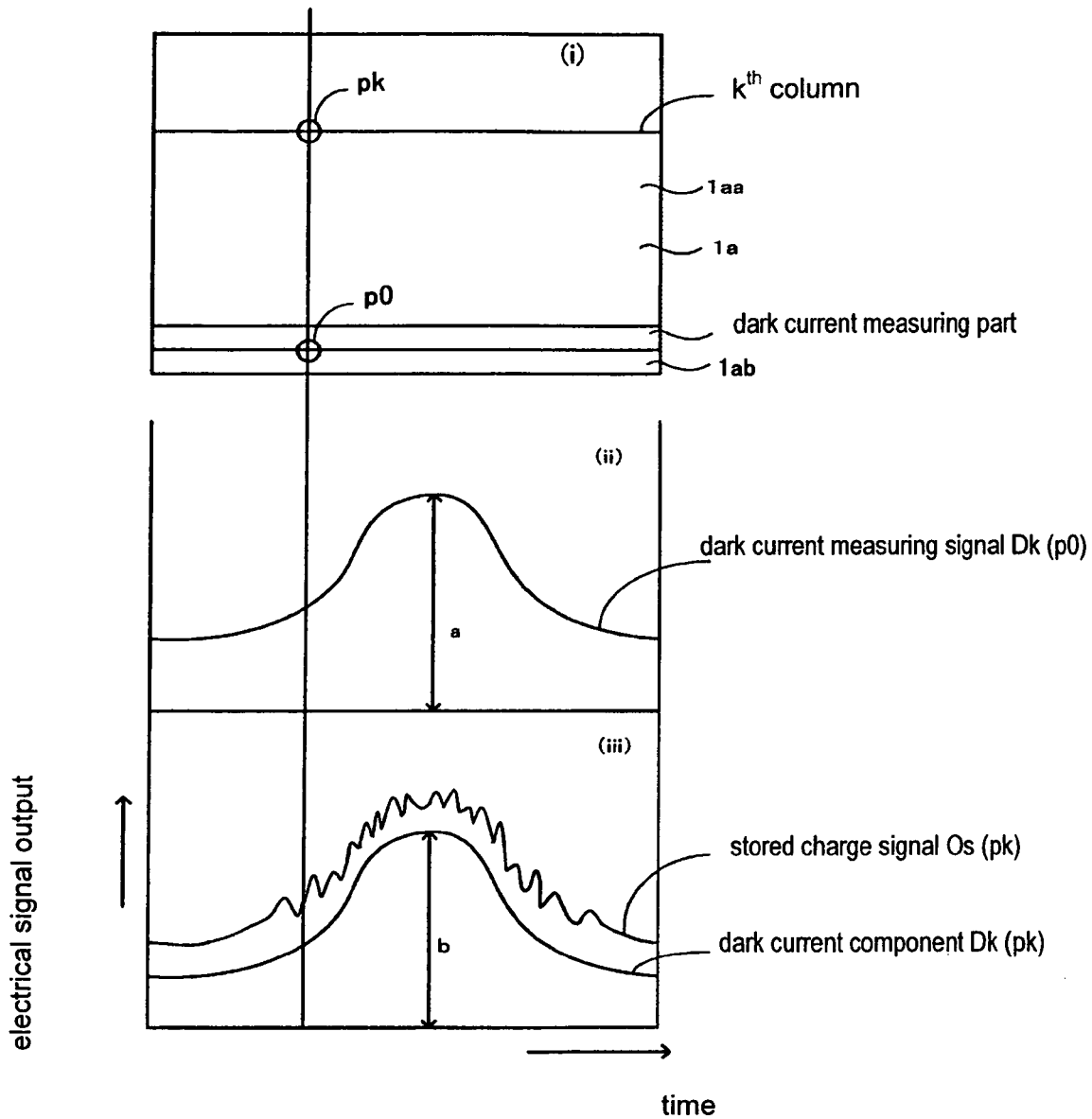
FIG. 2A is a comparison graph of output change of a dark current component of a notable pixel element and that of a dark current measuring part in case of panoramic radiography.
Figure 2B:
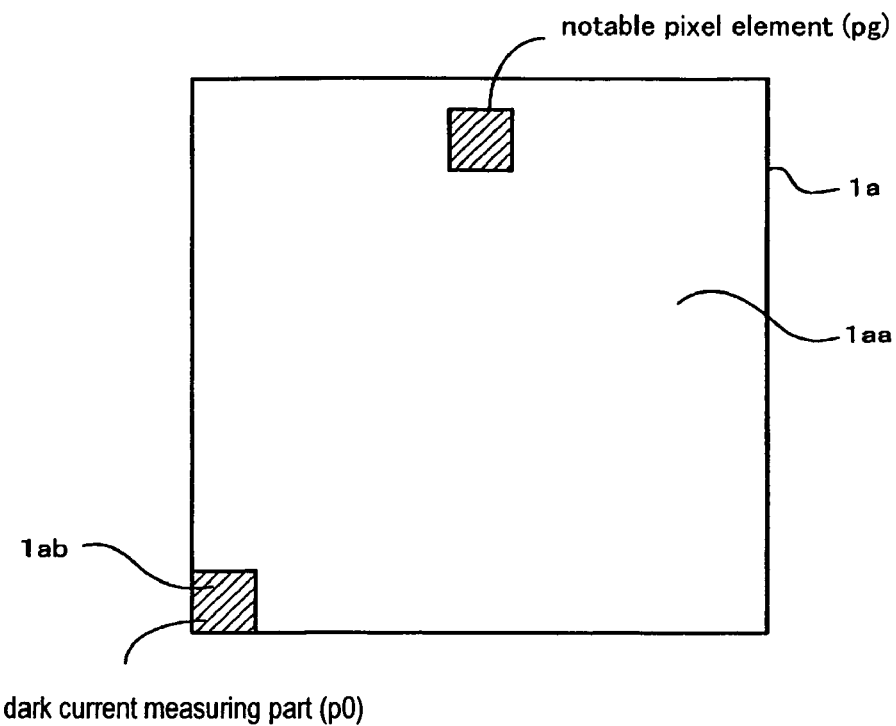
FIG. 2B is a graph showing the relation of a dark current component and an exposure time T in case of normal X-ray transmission radiography.
Figure 2B:
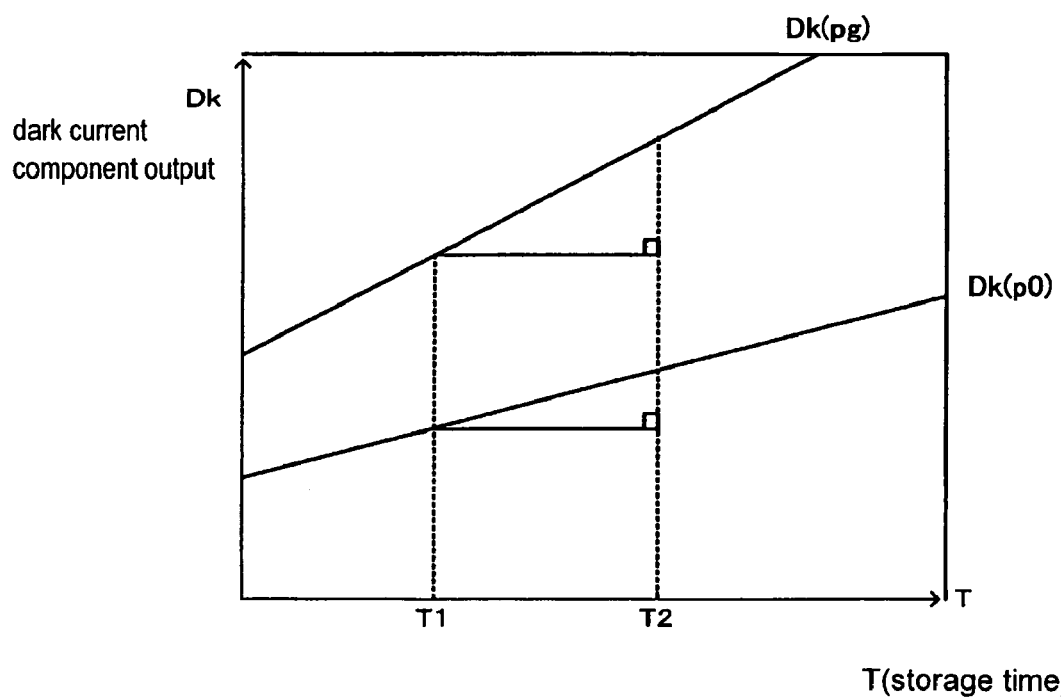

The principle of the above-mentioned automatic exposure control is further explained referring to FIG. 2 in case of a panoramic radiography by means of the solid-state image sensing device 1a with CCD sensor and in case of a normal X-ray transmission radiography by means of the solid-state image sensing device 1a with MOS sensor.

FIG. 2A shows the relation of the time and the electric signal output in case of a dental panoramic radiography wherein the stored charge signals (one dimensional) outputted from each column of the solid-state image sensing device 1a with CCD sensor are arranged in a time series of radiography. In the figure (i), the position of a specified pixel element, namely the notable pixel element 1ag in the picture element producing part 1aa is shown with the reference pg and the position of the dark current measuring part 1ab is shown with the reference p0. The figure (ii) shows the dark current measuring signal (dark current component) Dk(p0) from the dark current measuring part 1ab. It shows the dark current measuring signal in the dark current measuring part 1ab when X-ray panoramic radiography is executed in advance before factory shipment. Figure (iii) shows the stored charge signal Os(pg) from the notable pixel element 1ag in case of actual radiography and the dark current component Dk(pg) therein.

As understood from the figures (ii) and (iii), in case of a panoramic radiography from a cheek tooth, a front tooth, to a cheek tooth of an object to be examined, the scanning speed of panoramic radiography for the front tooth is generally reduced to increase the X-ray amount and the X-ray absorption into cervical vertebrae is compensated. In such a case the dark current component Dk(pg) is increased corresponding to the scanning speed. However, the output ratio of the dark current measuring part 1ab and the dark current component of the notable pixel element 1ag is constant irrespective of the absolute strength variation. Namely, the output ratio b/a is constant in the figures.

Accordingly, the output ratio of dark current component of the dark current measuring part 1ab and the notable pixel element 1ag for a predetermined exposure time is stored in the dark current compensation table 3 in advance, the dark current component Dk(pg) can be expected and calculated by applying the corresponding output ratio for the stored charge signal Os(pg) taken out of the notable pixel element 1ag in case of radiography. Therefore, the exposure measuring signals can be calculated in which the dark current component Dk(pg) is removed from the stored charge signals Os(pg), and the automatic exposure control is achieved based on the calculated signals.

FIG. 2B (iv) shows the position pg of a specified pixel element, namely the notable pixel element 1ag, and the position p0 of the dark current measuring part 1ab on the image in which the stored charge signal Os(pk) outputted from the solid-state image sensing device 1a with MOS sensor is arranged two dimensionally responsive to the position of the pixel element "e". FIG. 2b (v) is a graph showing the relation of dark current component Dk (pg) at the position of the notable pixel element 1ag, the dark current component Dk(p0) at the position of the dark current measuring part 1ab, and the exposure time T.

As shown in the graph (v), the inclination ratio of the output change of the stored charge signal Ok(pk) of the notable pixel element 1ag for the exposure time T and the output change of the stored charge signal Dk(p0) of the pixel element or at least one pixel element column in the dark current measuring part 1*ab* for the exposure time T is substantially constant. Therefore, when the inclination ratio of those output changes is stored in advance in the dark current compensation table 3 corresponding to each pixel element or each pixel element column in the picture element producing part 1*aa*, the corresponding output change inclination is applied to the stored charge signal Ok(pg) taken out of the notable pixel element 1*ag* in case of radiography and the dark current component Dk(pk) can be expected and calculated responsive to the actual radiography time. Therefore, the exposure measuring signals from which the dark current component Dk(pg) is removed is calculated and the automatic exposure control is executed based on the calculated signals.

FIG. 3 shows one example of the dark current compensation table 3. In the figure, $\alpha 2(pk=1 \ldots n)$ indicates the output ratio $\alpha 2$ in a predetermined exposure time for the dark current measuring signal of each column (k=1 . . . n) in the picture element producing part 1*aa*. When the output ratio is stored for each column, the notable pixel element 1*ag* may be set at an optional position in the picture element producing part 1*aa*.

Here, the operations of feedback control of the control processing means 2 for a drive current I is explained referring to the attached figure.

Figure 4:
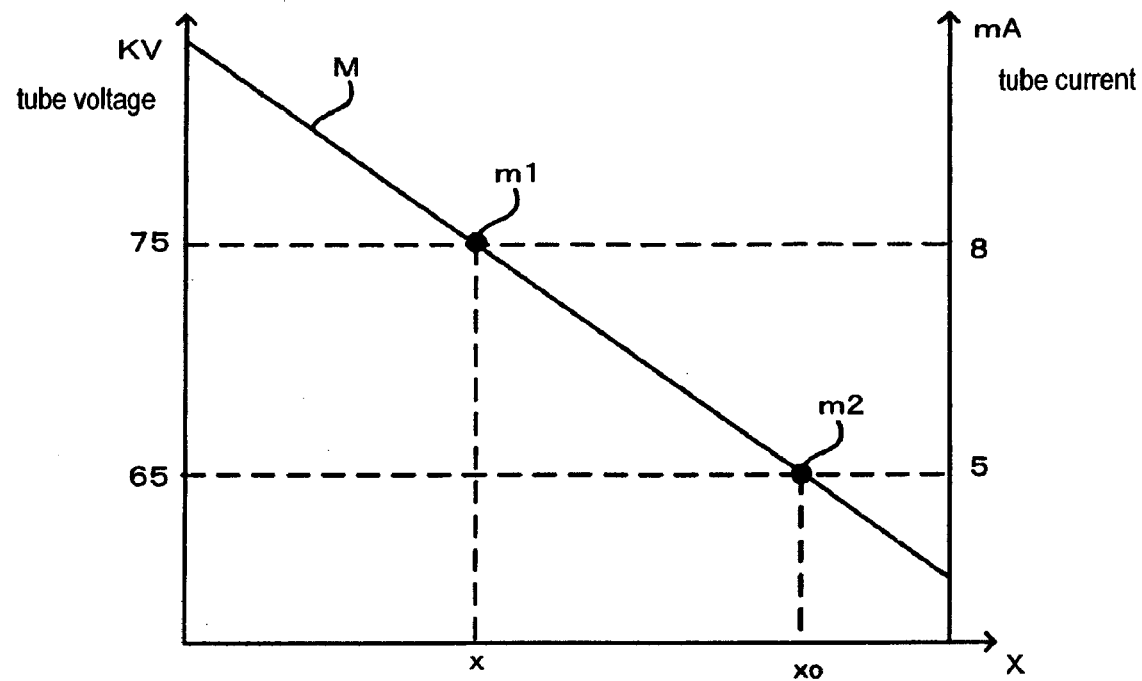
FIG. 4 is a graph showing the relation of exposure control signals and a drive current.

FIG. 4 is a graph showing the relation of the exposure control signals X and the drive current I. This explanation is qualitative and the coordinate and inclination of the graph may be optional. In the figure, the line M indicates the aforementioned formula (VII) I=−AX+B (X is exposure control signal, A, B is an optional constant value respectively). This feedback controlled is executed so as to keep, within a predetermined density range, the amount value which is defined by removing the charge signals stored on a specified pixel element or a specified pixel element column in said dark current measuring part of said image sensing device from the charge signals stored on a specified pixel element or a specified pixel element column in said picture element producing part of said image sensing device. The drive current I is a function of the exposure control signals X and is expressed with a straight line, however, it is actually a monotonous increasing function and it may be a curved line. Here, the drive current I may be a tube current or a tube voltage in case of X-ray control. Further, it may be any one of the scanning speed and the gradation process or be a combination thereof.

It is understood that when the drive current I is increased, the value of stored charge signal Os(pk, $\xi$) in the picture element producing part 11*a* is wholly increased, and as the result, the stored charge signal Os(pg, $\xi$) of the notable pixel element is increased. However, the dark current measuring signal Os(p0, $\xi$) does not change because the storage time T is not changed.

In FIG. 4, when the value "x" of exposure control signal X is the point m1 on the line M in case of actual radiography, the control is executed aiming for the point m2 of the target exposure control signals x0.

When the stored charge signals of notable pixel element are out of the control target value and are promptly converged to the control target value, the part causes dark and light stripes comparing to the other parts.

Such a problem can be solved by adding a predetermined delay element to feedback control and slowly following the control target value (acting as a low pass filter). Practically, a low pass filter by means of a condenser and a resistance may be arranged, or a time attenuation factor is weighed on a past value to add on a present value.

Next, diagrammatical procedures of producing the dark current compensation table and the automatic exposure control are explained following flow charts.

Figure 5A:
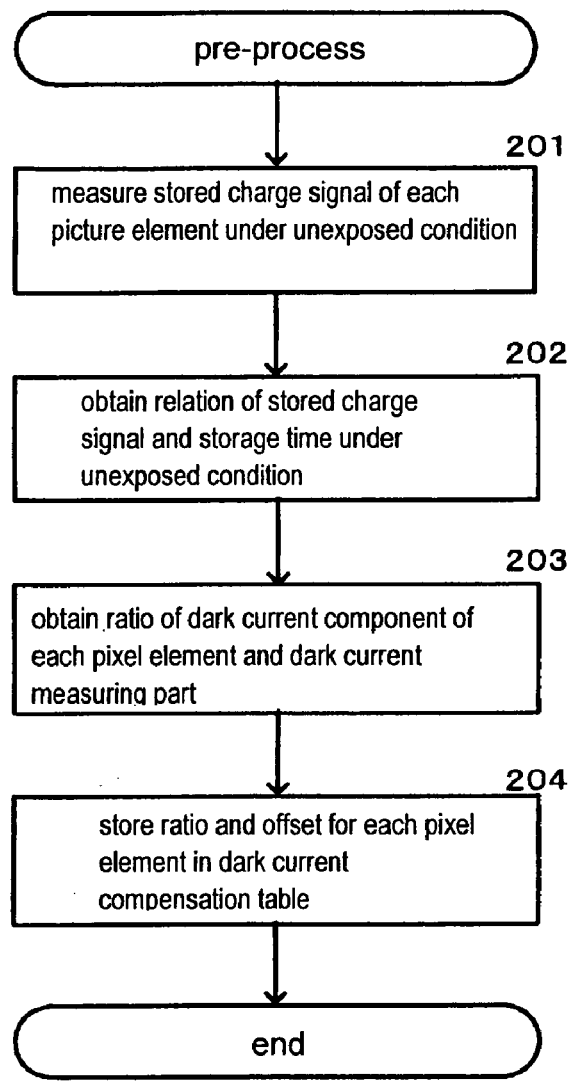
FIG. 5A is a flow chart showing how a compensation table is produced.

FIG. 5A shows how the dark current compensation table 3 is produced before an actual radiography, for example before factory shipment. At step 201, the solid-state image sensing device 1*a* is entirely shielded and the stored charge signal Os(pg) for the entire pixel element including the dark current measuring part 1*ab* for plural storage times T are measured. At step 202, the relation of the storage time T and the stored charge signal Os(pg) for all the pixel element is obtained from the measured result. Then at step 203, the output ratio $\alpha 2$ of the dark current component for a predetermined exposure time of the dark current measuring part 1*ab* and each pixel element or each pixel element column in the picture element producing part 1*aa* is obtained from the obtained relation of the storage time T and the stored charge signal Os(pg) for all the pixel element. Finally at step 204, the output ratio $\alpha 2$ and the offset Of are stored in the dark current compensation table 3 relative to all the pixel element. The dark current compensation table 3 is stored for plural kinds of storage time in which the temperature is changed, if necessary.

Figure 5B:
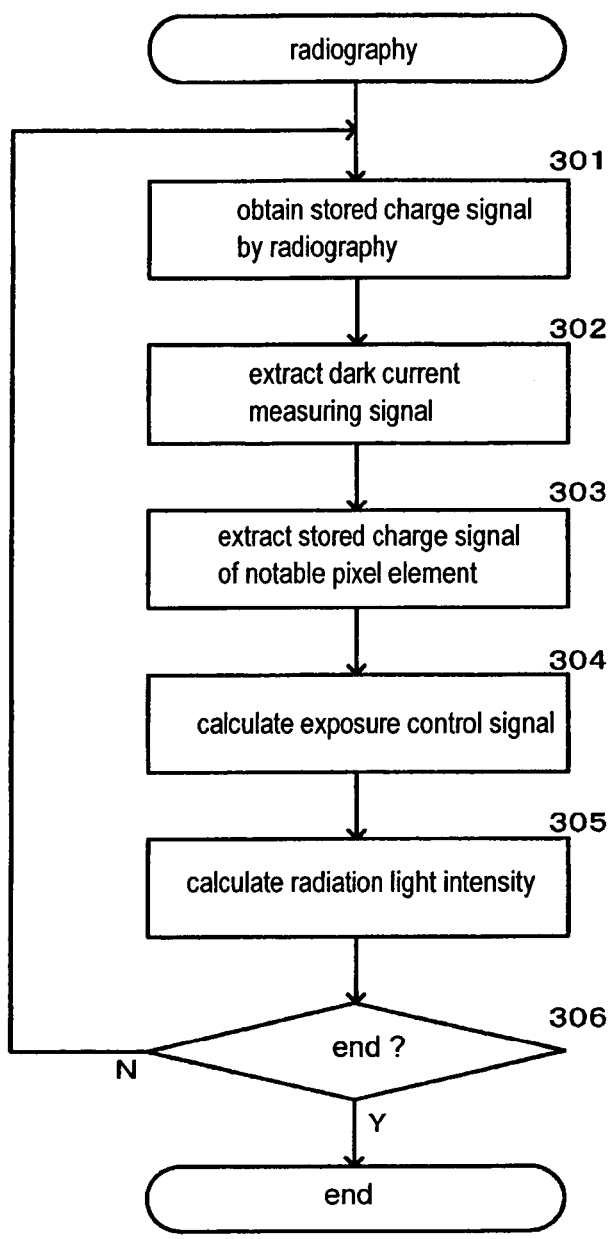
FIG. 5B is a flow chart showing the procedure of an automatic exposure control method.

FIG. 5B shows the automatic exposure control procedure in case of actual radiography. At step 301, radiography is executed and the stored signals Os for each pixel element are outputted. At step 302, the dark current measuring signal Os(p0) is extracted. Next at step 303, the stored charge signal Os(pg) from the notable pixel element 1*ag* is extracted. The extracted stored signal Os(pg) of the notable pixel element may be one column signal or plural column signals. At step 304, the value $\alpha 2(pk)$ stored in the dark current compensation table 3 is applied to the dark current measuring signal Os(p0) and the stored charge signal Os(pg) to calculate the exposure control signal X. At step 305, the intensity of radiation light which is a target value to be controlled is calculated based on the exposure control signal X and feedback control is executed at the same time of radiography. The last step 306 judges whether the process is finished, and if the procedure is not finished, the step is returned to 301. Actually, the dark current component of the exposed pixel element is expected from the relation of the exposed pixel element and the unexposed pixel element for the charge storage time stored in the compensation table per a pixel element in advance in case of radiography, and from the relation of the radiography time measured during actual radiography and the unexposed pixel element, and feedback control is executed by the exposure control signals. For this expectation, the charge storage time during pre-process and that during radiography are not used as a parameter. Therefore, the extracting process of the charge storage time is not required, thereby being applicable when a TDI clock generator is provided out of an X-ray detector. In the feedback control of radiography, any one of the X-ray scanning speed, an X-ray tube current, an X-ray tube voltage and a gradation process, or a combination thereof is practically controlled.

EMBODIMENT 2

Next explained is a medical digital X-ray imaging apparatus capable of panoramic radiography in which the present invention is applied.

Figure 6:
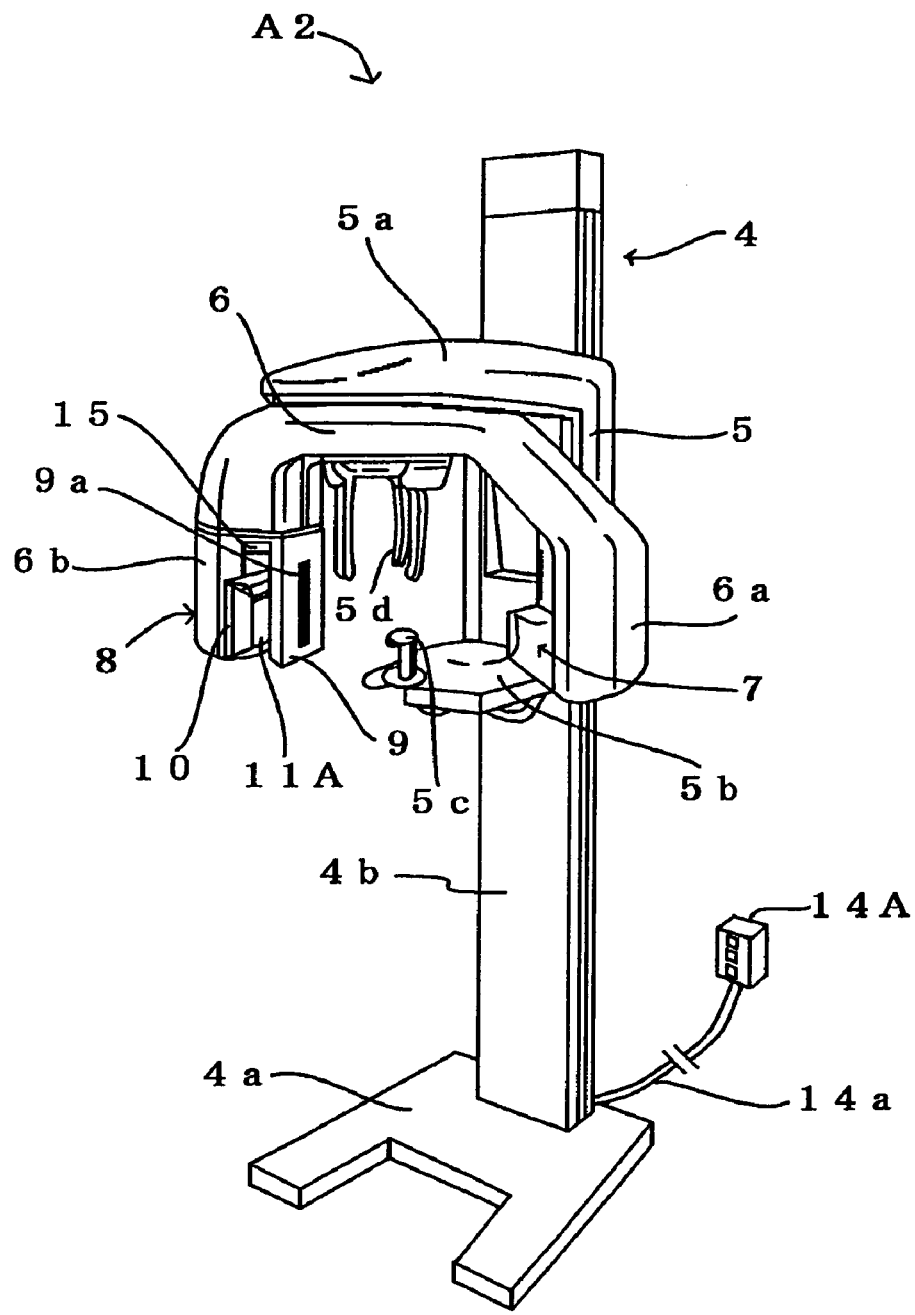
FIG. 6 is an external view of a medical digital X-ray imaging apparatus capable of panoramic radiography when the present invention is applied.

FIG. 6 shows is an external view of the X-ray imaging apparatus A2. A brace 4*b* stands on a base 4*a* of an apparatus body 4, a support body 5 is attached to the brace 4*b* so as to be movable up and down, and a rotary arm 6 is rotatably provided for the support body 5. A support arm 5*a* extending horizontally is provided for the upper end of the support body 5 and an object frame 5b is provided for the lower end thereof. A chin rest 5c is provided for the object frame 5b.

XY table which is movable in X and Y directions by means of a step motor is housed in the support arm 5a and the rotary arm 6 can be rotated while being suspended via the XY table and moving freely in the vertical plane. Head holding means 5d for object is an object holding means fixed to the lower face of the support arm 5a penetrating the rotary arm 6 and has a position control mechanism.

Turning mechanism is provided for the rotary arm 6 to turn the rotary arm 6 with respect to the support arm 5a with a step motor. The rotary arm 6 is constructed such that it turns with respective to a perpendicular axial line while moving the rotary center by means of the above-mentioned XY table. The both ends of the rotary arm 6 hangs down, an X-ray generator 7 is provided for one end 6a and an X-ray detecting part 8 is provided for the other end 6b so as to oppose each other. The X-ray generator 7 has an X-ray tube, an X-ray shielding plate with a first longitudinal slit, a control mechanism for changing the shape of the first slit, and so on (they are not shown).

The X-ray detecting part 8 has a second longitudinal slit 9a corresponding to the first slit and a shielding plate 9 with a control mechanism for the slit 9a, which are provided so as to oppose the X-ray generator 7. Detector holder 10 is provided at the back of the shielding plate 9 and a detector 11A for radiography is mounted on the detection holder 10.

Controlling part 12 for the apparatus body having a print board incorporating several circuits is provided behind the X-ray detecting part 8 and an operation panel 13 is provided so as to cover the outside thereof. Several switches and a liquid crystal display 13a are provided for the operation panel 13 (not shown).

The apparatus body 4 has a remote control box 14A connected with an operation code 14a and a main switch for turning on or off an electric source and an X-ray radiation switch are provided for the box 14A. Connector 15 is provided for the X-ray detecting part 8 for connecting to the detector for radiography.

Figure 7:
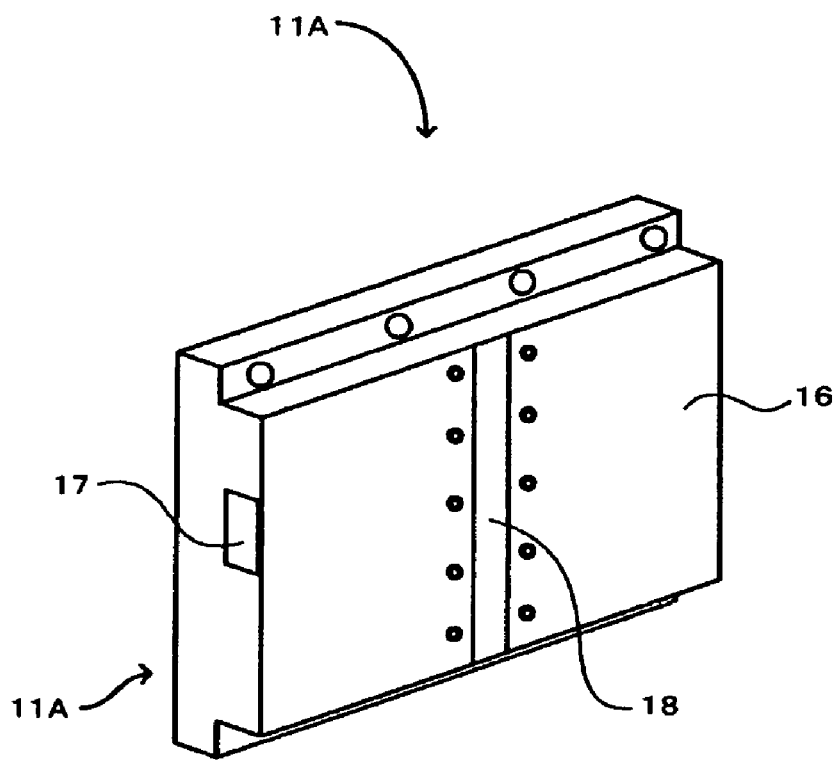
FIG. 7 is an external view of a detector for radiography which constitutes the medical digital X-ray imaging apparatus of FIG. 6.
Figure 8:
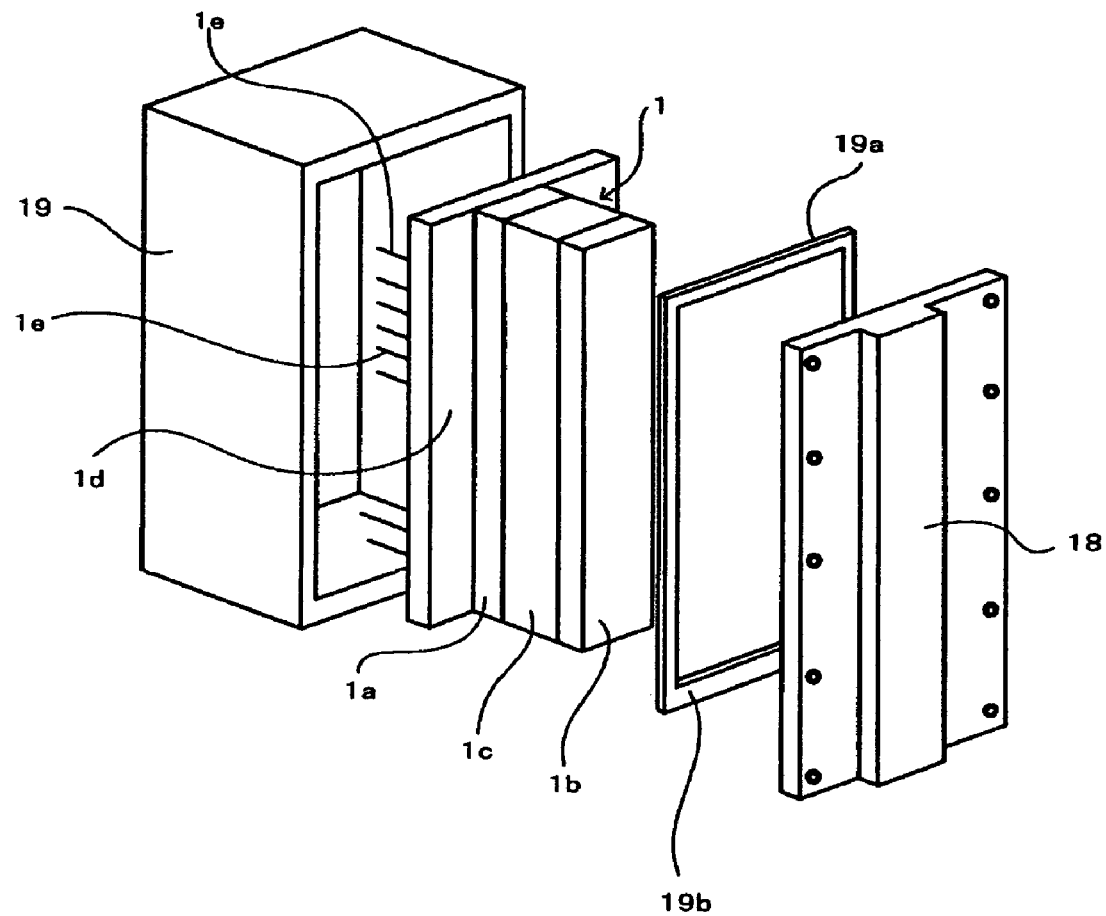
FIG. 8 explains the inner structure of the detector for radiography of FIG. 7.

FIG. 7 shows the external view of the detector 11A for radiography and FIG. 8 shows the inner structure thereof. The detector 11A includes a solid-state image sensing device unit 1 like CCD sensor and is armed with an outer housing 16 housing several kinds of circuits for the unit. Connector 17 for an outer circuit is provided on one side of the housing 16 and is generally connected with an unified cable of an electric supply line and a signal line (not shown) to the connector 15 of the X-ray detecting part 8. The connector 17 may be used for connecting to the external appliances such as a personal computer.

The outer housing 16 is made of a suitable material with necessary strength such as metal like an aluminum plate or a synthetic resin like ABS resin. X-ray receiving part 18 which is made of such material that preferably transmits X-rays but shields a visible light, for example ABS resin with dark color is longitudinally provided at the center of the front face so as to be back of the second slit 8a. The solid-state image sensing device unit 1 is provided inside of the X-ray receiving part 18.

The solid-state image sensing device unit 1 is provided on the reverse side of the X-ray receiving part 18, is comprised of a light emitting body 1b (scintillator) for converting the radiated X-rays into a visible light, an optical fiber 1c for transferring the light generated from the light emitting body 1b into the light receiving face of the solid-state image sensing device 1a, and the solid-state imaging sensing device 1a, which is explained later, and has a circuit board 1d. The reference numeral 19 indicates a protection case, 19a indicates a sealing material for shielding X-rays, and 1e is a signal pin of the solid-state image sensing device unit 1. X-ray shielding material 19b is attached at the lower part of the sealing material 19a, the X-ray shielding material 19b being a lead plate for setting the dark current measuring part 1ab, explained later, on the corresponding part of the solid-state image sensing device 1a by shielding the light emitting body 1b from X-rays.

Figure 9:
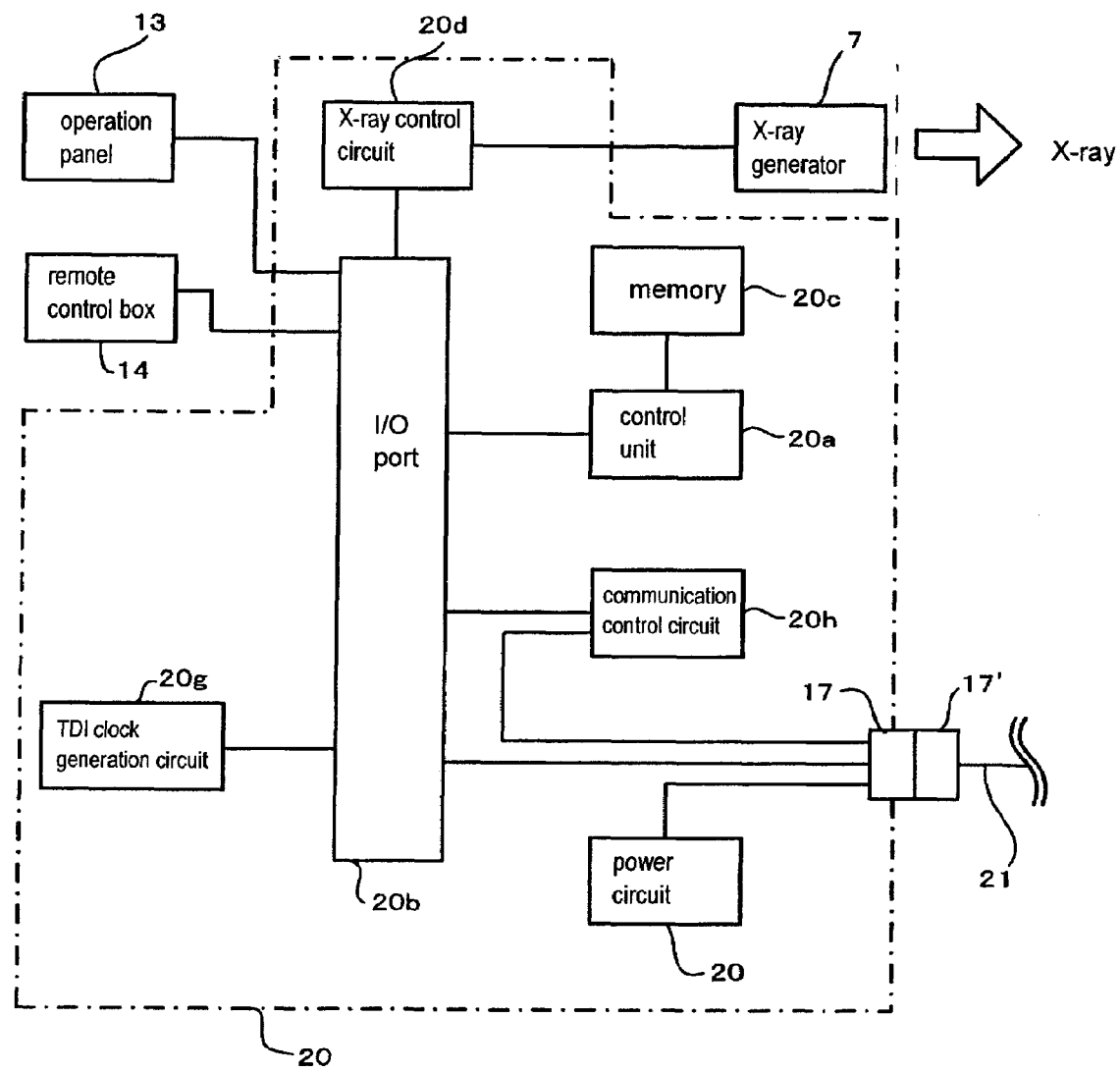
FIG. 9 is a block diagram showing the structure of a control part of a main body constituting the medical digital X-ray imaging apparatus of FIG. 6.
Figure 10:
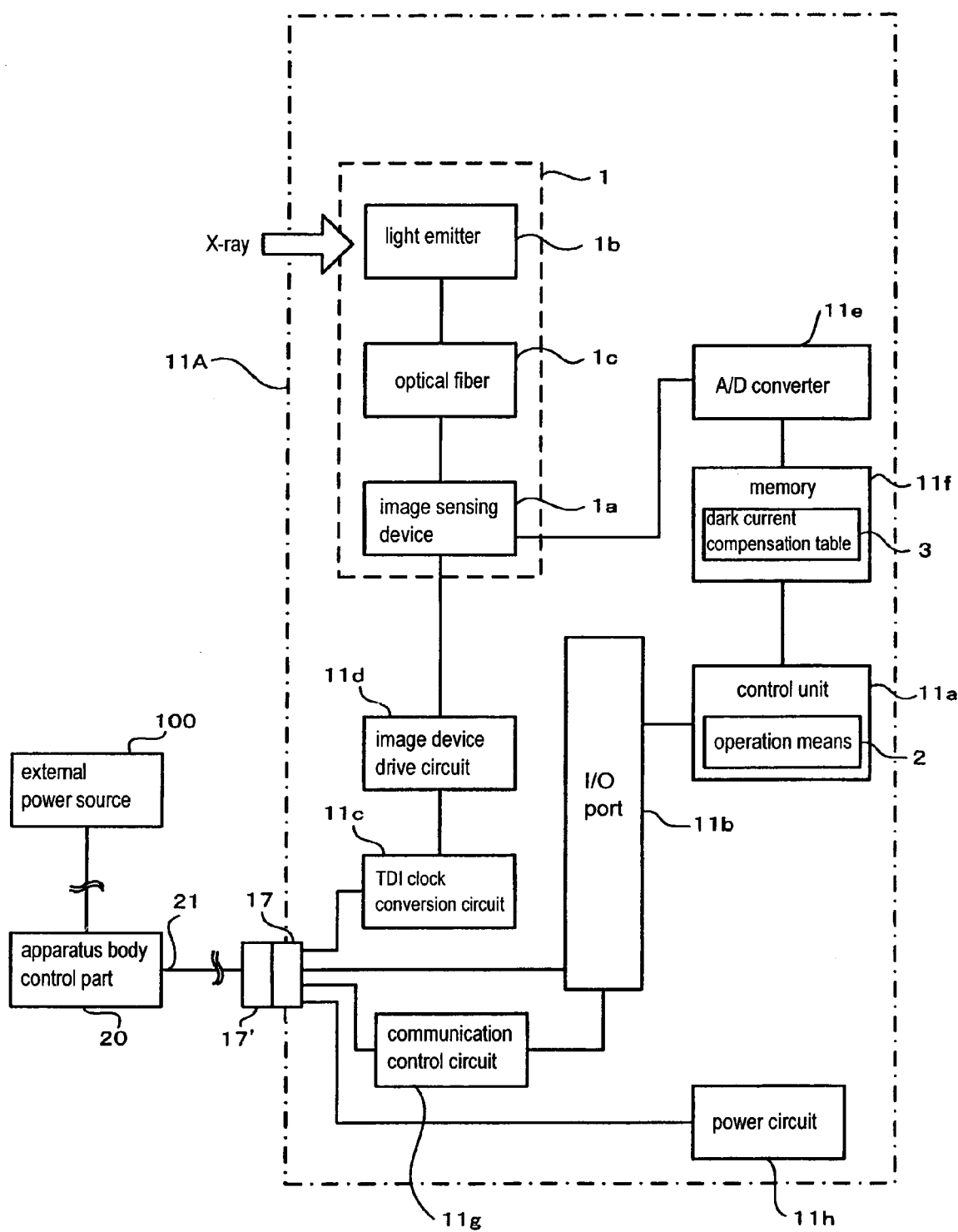
FIG. 10 is a block diagram showing the structure of a detector for radiography constituting the medical digital X-ray imaging apparatus of FIG. 6.

The diagrammatical structure of the essential part of the apparatus body 4 is explained referring to FIG. 9 and the diagrammatical structure of the essential part of the detector 11A for radiography is explained referring to FIG. 10.

FIG. 9 is a block diagram showing the diagrammatical structure of the essential part of the control part 20 of the apparatus body. The control part 20 has a control unit 20a comprised of MPU (CPU) being the center of operation and control of the entire X-ray imaging apparatus A2, an input/output port 20b and a memory 20c. In addition, it has an X-ray radiation control circuit 20d for driving and controlling the X-ray generator 7, an X-ray radiation detection circuit 20e, a rotary arm rotation detection circuit 20f, a TDI clock generation circuit 20g, a communication control circuit 20h, and a power circuit 20i. They are connected to the control unit 20a via the input/output port 20b. Operation panel 13 for inputting several operation data or a remote control box 14 for remotely inputting the data is connected to the input/output port 20b. Further provided is a connector 15 corresponding to the connector 15' of a connection cable 21 for connecting the detector 11A for radiography and the input/output port 20b, the communication control circuit 20h and the power circuit 20i are connected to the connector 15.

FIG. 10 is a block diagram of the essential part of the detector 11A for radiography. The detector 11A has a control unit 11a comprised of MPU (CPU) for controlling the operation of each circuit in the detector 11A and the entire operation of the X-ray imaging apparatus A2 including the apparatus body 4 by itself or together with the control part 20 of the apparatus body, an input/output port 11b, a TDI clock conversion circuit 11c, an image element driving circuit 11d, an A/D converter 11e, a memory 11f, a communication control circuit 11g, and a power circuit 11h. Each circuit and a connector 17 are connected as shown in the figure. The control unit 11a is constructed so as to bring out the function of the operation control means 2 for automatic exposure control, which is explained as the characteristic of the present invention in Embodiment 1, by means of a software process. The dark current compensation table 3 for which the picture element processing means refers is stored in the memory 11f in advance before factory shipment and is used for storing the effective pixel element producing a panoramic X-ray image during radiography.

The detector 11A for radiography is constructed so as to be detachable or fixedly attached to the apparatus body 4. For the purpose, the connector 17 is electrically and regulatory connected to the control part 20 of the apparatus body by means of a connector 17' provided for the connection cable 21 introduced from the control part 20 of the main body. The control part 20 of the apparatus body is constructed such that an external appliance 100 such as a personal computer is connected so as to input control information into the control part 20 itself and the detector 11A of the radiography and to output and store the data. The memory 11f in which the dark current compensation table 3 is stored is provided in the detector 11A for radiography in the above-mentioned embodiment, however, the memory in the computer provided out of the apparatus body may be used.

Figure 11:
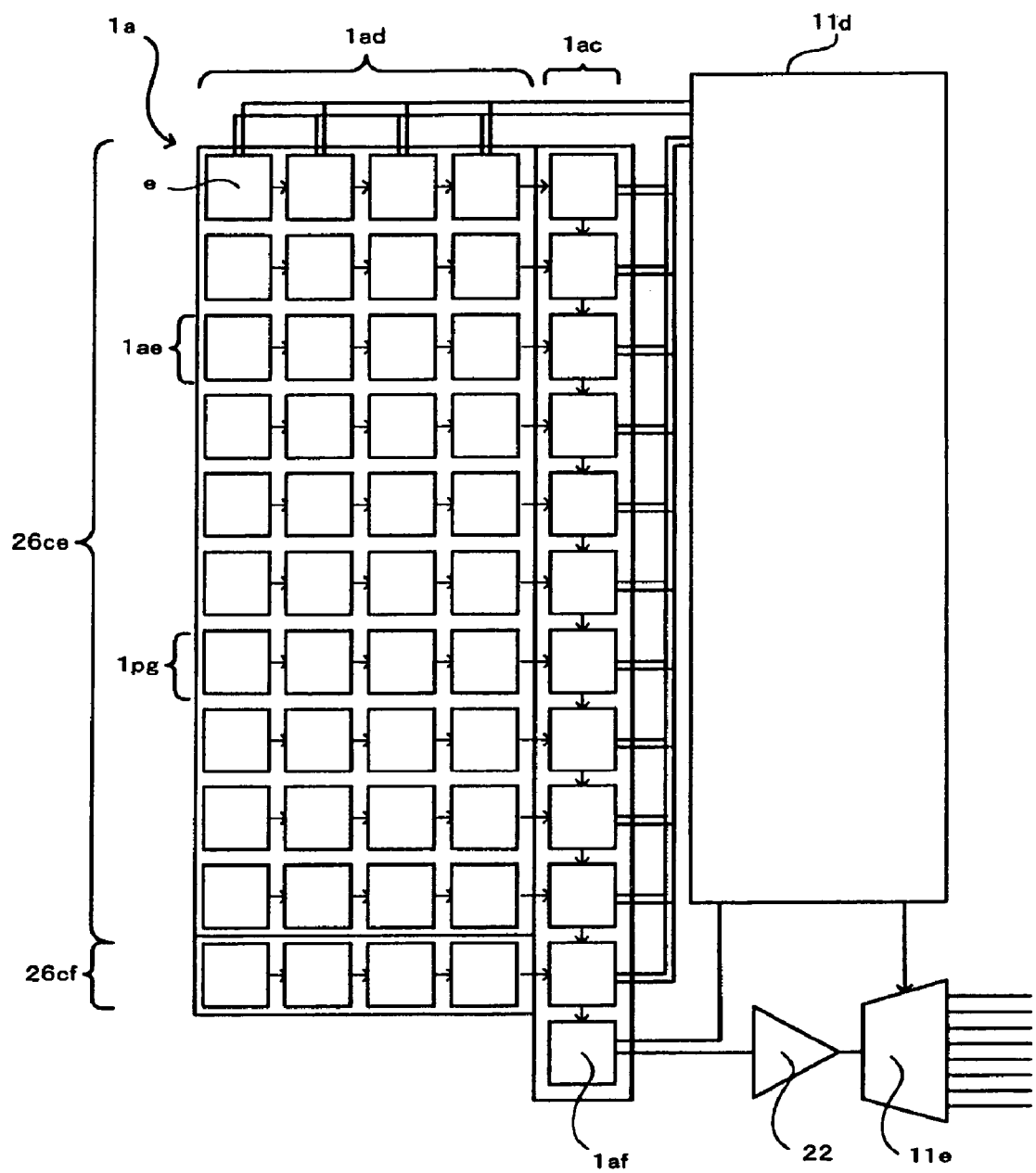
FIG. 11 shows the structure of solid-state image sensing device of FIG. 9.

FIG. 11 shows a diagrammatical structure of the solid-state image sensing device 1a provided for the detector 11A for radiography. The solid-state image sensing device 1a is comprised of CCD sensor of FFT type (Full Frame Transfer Type). The reference numeral 1ad indicates a sensor matrix consisting a light receiving part and is constructed such that a horizontal shift register 1ae for transferring the stored charge in horizontal direction is arranged in plural columns up and down and a pixel element "e" arranged in a column or step is formed by the potential well formed in the horizontal shift register part 1ae.

The reference numeral 1ac is a stored charge transferring part for forming a potential well which perpendicularly transfers the stored charge transferred in parallel in horizontal direction at once through the potential well of each horizontal shift register part 1ae which is formed in plural columns up and down, 1af indicates an output well for taking out the stored charge serially transferred in vertical direction from the stored charge transferring part 1ac, and 22 indicates an amplifier for further converting the stored charge sequentially outputted from the output well 1af into voltage signals to output as the stored charge signals.

In the sensor matrix 1ad, the pixel element "e" is arranged in 11 columns (vertical direction) and in 4 steps (horizontal direction) in the figure, however, the pixel element "e" is actually arranged in 1500 columns and 64 steps. The picture element producing part 1aa for outputting the pixel element forming the image as stored charge is allocated at the columns other than the lowest column in the figure, and the lowest column is allocated with a dark current measuring part 1ab which is always under unexposed condition by shielding X-rays with the X-ray shielding member 19b and outputs the dark current measuring signals as stored charge. Further, the notable pixel element 1ag is set in the picture element producing part 1aa.

The stored charge signals outputted from the amplifier 22 are sent to the AD converter 11e to be converted into digital signals. The horizontal shift register 1ae, the stored charge transferring part lac and the output well 1af which comprise CCD sensor transfer the stored charge following the driving clock of the imaging sensing device drive circuit 11d.

JP-A-9-200625 has disclosed such a basic operation of charge transfer of CCD sensor that the stored charge obtained by emitting light is blocked in the potential well of the sensor matrix 1ad constituting a light receiving surface to be transferred in a semiconductor material. However, the structural characteristic of the solid-state image sensing device 26c is the dark current measuring part 1ab which is always unexposed condition and outputs dark current measuring signals as stored charge is allocated to a part of the sensor matrix 1ad, and further the notable pixel element 1ag is set at an appropriate position in the picture element producing part 1aa for automatic exposure control. The CCD sensor explained above is a full frame transfer type, however, it may be FT type (Frame Transfer type). Further, the sensor may be a solid-state image sensing device such as MOS sensor, C-MOS sensor, a two-dimensional flat panel sensor like TFT (Thin Film Transistor), and so on in place of the above-mentioned CCD sensor. Still further, a visible light from the light emitting body 1b for converting the radiated X-rays into a visible light is received in the above-mentioned embodiment, however, CCD sensor which directly detects X-rays may be used.

Figure 12A:
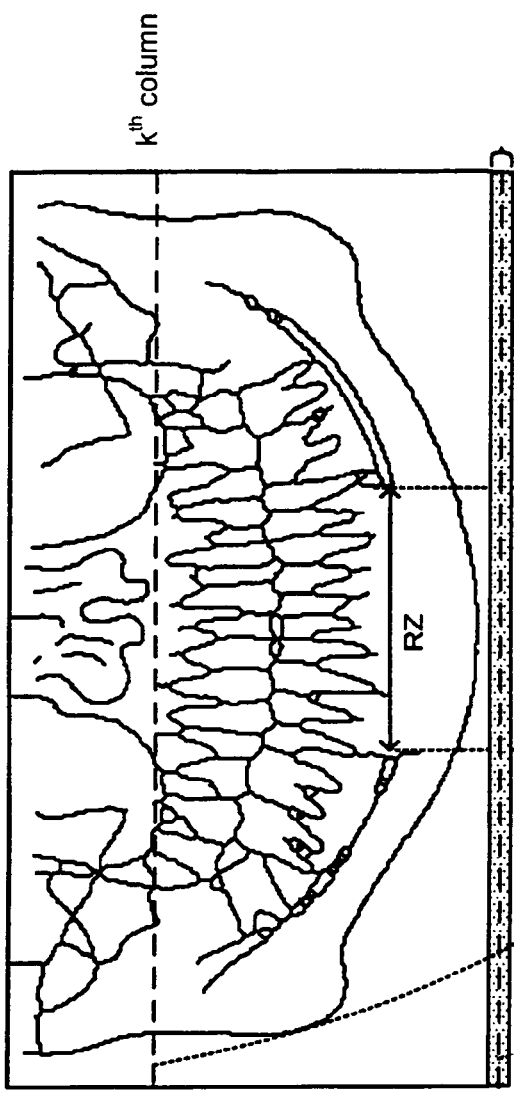
FIG. 12 is a panoramic X-ray transmitted image obtained by the medical digital X-ray imaging apparatus of FIG. 6.
Figure 12B:
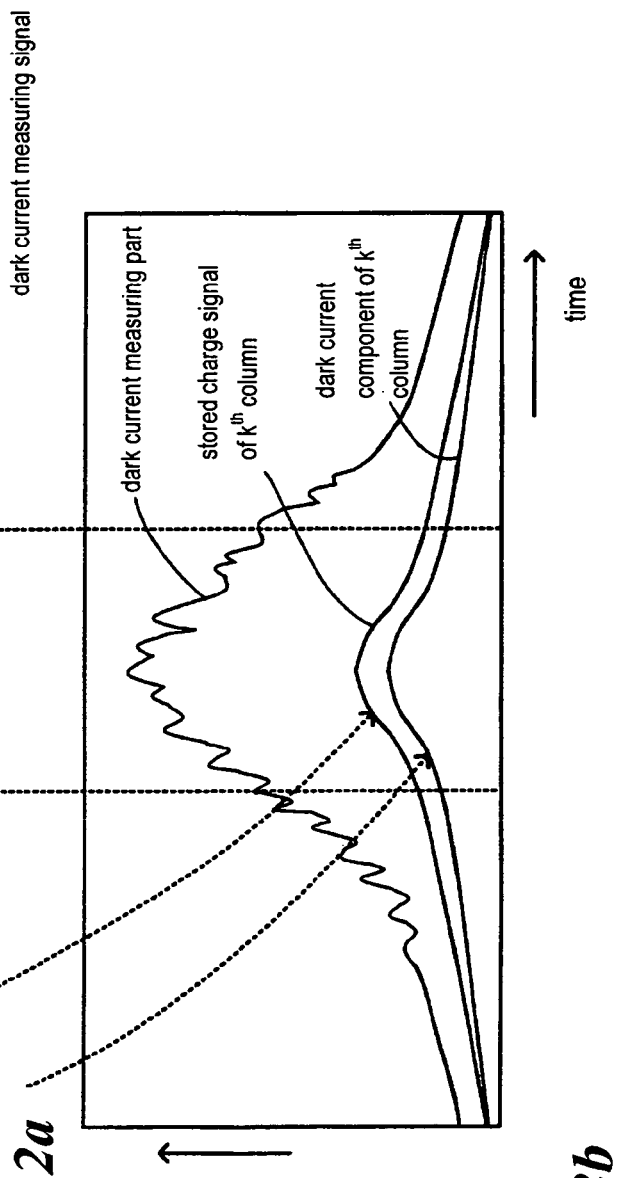

FIG. 12 shows one example of a panoramic X-ray image obtained by thus constructed panoramic X-ray imaging apparatus A2, FIG. 12a is a panoramic X-ray transmitted image of the entire jaw and FIG. 12b is a graph showing the stored charge signals from the notable pixel element 1ag suitably positioned in the picture element producing part 1aa and the dark current measuring signals from the dark current measuring part 26cf.

The reference RZ in FIG. 12a indicates a density compensation area generally used for panoramic radiography. X-rays are radiated for a longer time in the area in order to remove the effect of obstacle shade like cervical vertebrae and the rotary arm 6 turns slowly for the purpose.

As understood from FIG. 12b, there is a large amount of dark current measuring signals in the density compensation area. The dark current component in the stored charge signals from the notable pixel element 1ag and the dark current measuring signals from the dark current measuring part 1ab have different absolute strength, however, the strengths have a proportional relation.

According to the method explained in the Embodiment 1, based on the dark current measuring signals from the dark current measuring part 1ab, the dark current component in the stored charge signals from the notable pixel element 1ag is expected and calculated to be removed, thereby obtaining the exposure control signals. The feedback control can be executed in such a manner that the intensity of exposure control signals become uniform.

CCD sensor is used as a solid-state image sensing device 1a in this embodiment, however, MOS sensor in which a photo diode of each pixel element is selected by MOS transistor and the electric charge is taken out may be used in place of CCD sensor.

EMBODIMENT 3

Next explained is an embodiment wherein the present invention is applied to a medical digital X-ray imaging apparatus capable of cephalometric radiography.

Figure 13:
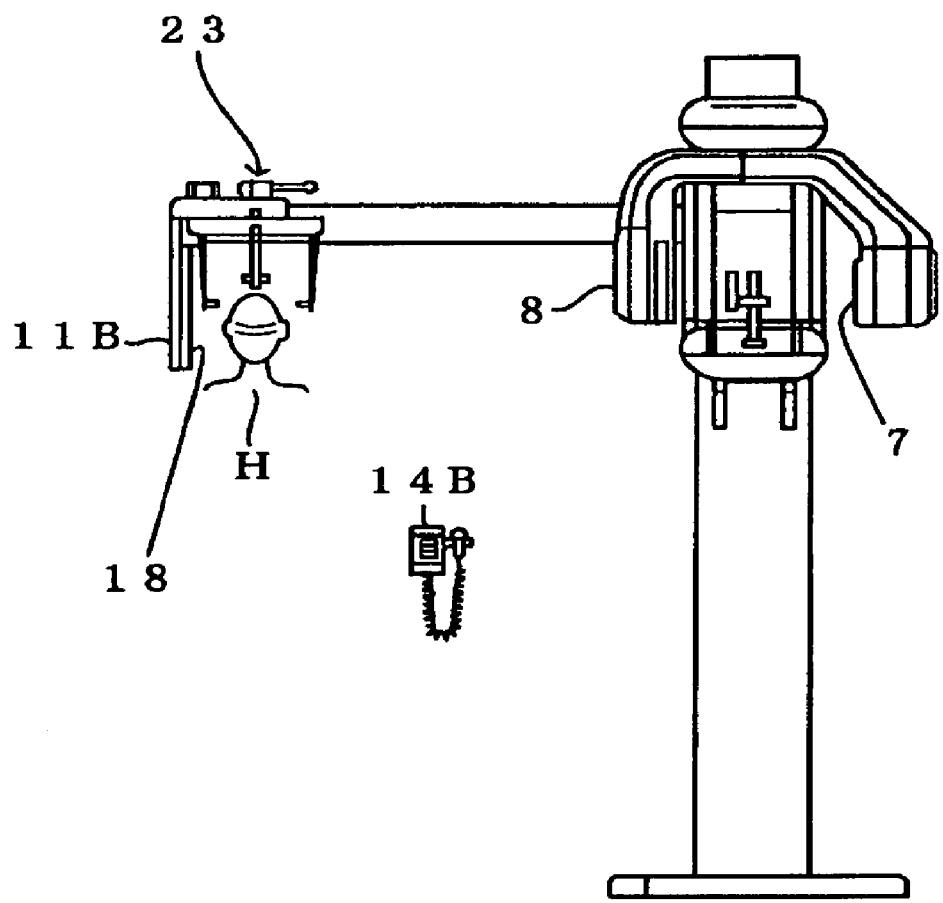
FIG. 13 is an external view of a medical digital X-ray imaging apparatus capable of a cephalometric radiography when the present invention is applied.

FIG. 13 is an external front view of the X-ray imaging apparatus A3. The X-ray imaging apparatus A3 is constructed such that the X-ray imaging apparatus A2 of FIG. 6 which is explained in Embodiment 2 is further detachably provided with a detector 11B for radiography for cephalometric radiography. In addition, a support apparatus 23 for cephalometric radiography to support a head H of an object to be examined is provided, thereby enabling a cephalometric radiography as well as a panoramic radiography.

The detector 11B for radiography has the same structure as that of the detector 11A for radiography which is used for the X-ray imaging apparatus A2 of the Embodiment 2. Remote control box 14B has the same structure as the remote control box 14A in FIG. 6, however, the setting position and capable operations are changed in order to be used for both a panoramic radiography and a cephalometric radiography.

In case of cephalometric radiography, like the prior art, the X-ray detecting part 8 is out of the X-ray radiation area of the X-ray generator 7, the X-rays from the X-ray generator 7 transmit the object's head H fixed with the support apparatus 23 for cephalometric radiography, and they reach the detector 11B for radiography. At this time, the detector 11B for radiography is movable up and down or right and left with respective to the support apparatus 31 for cephalometric radiography in such a manner that the X-ray receiving part 18 can receive the X-ray transmitted image of the entire object's head H.

Figure 14:
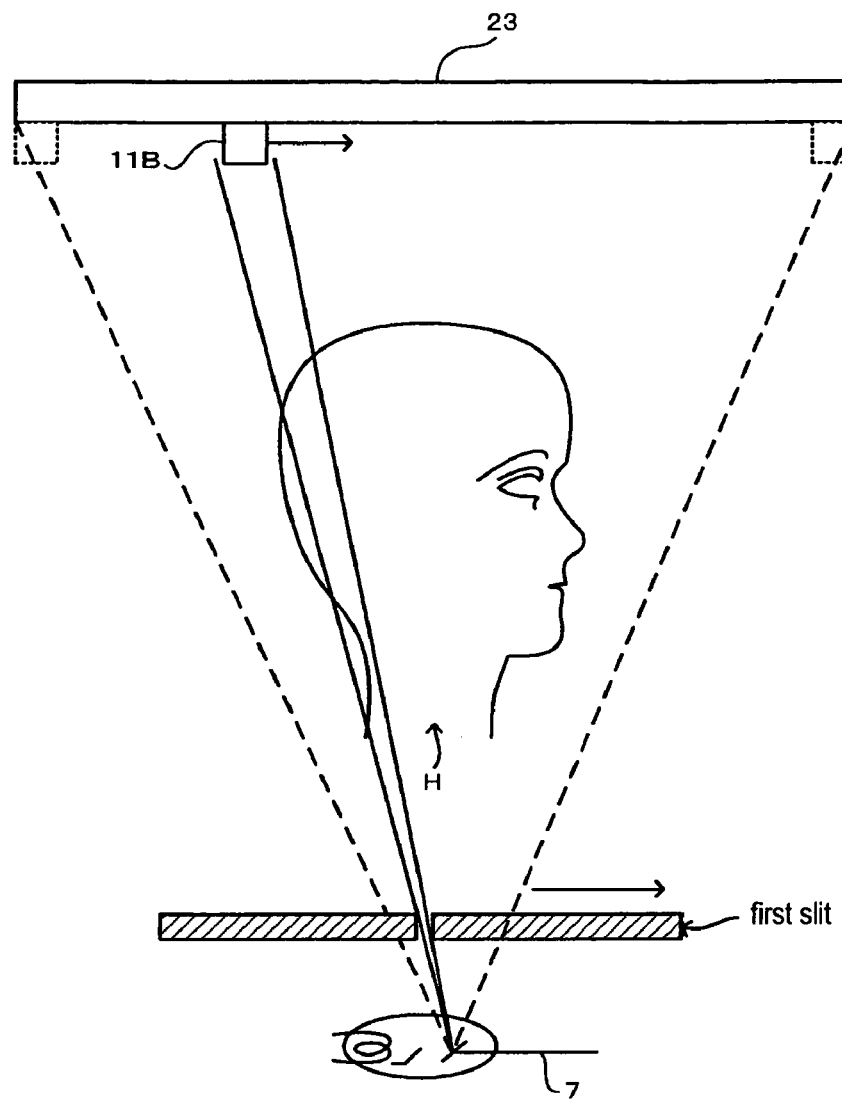
FIG. 14 shows the positional relation of an X-ray generator, an object to be examined and a detector for radiography in case of a cephalometric radiography.

FIG. 14 shows the positional relation of the X-ray generator 7, the head H of the object, and the detector 11B for radiography in case of a cephalometric radiography. As shown in the figure, the radiation area of the X-rays radiated from the X-ray generator 7 is limited into the like a pyramid by a first slit. The first slit and the detector 11B for radiography are cooperatively moved in right and left directions in such a manner that the X-ray beam transmits the head H of the object and the detector 11B for X-ray radiography receives the X-ray transmitted image of the entire head H.

In case of such cephalometric radiography, the detector 11B for radiography provided for the X-ray imaging apparatus A3 has the same structure as the detector 11A for radiography provided for the X-ray imaging apparatus A2 in the Embodiment 2, so that the automatic exposure control can be executed according to the method explained in the Embodiment 1.

EMBODIMENT 4

Now explained is an embodiment wherein the present invention is applied to a medical digital X-ray imaging apparatus capable of a linear scan radiography.

Figure 15:
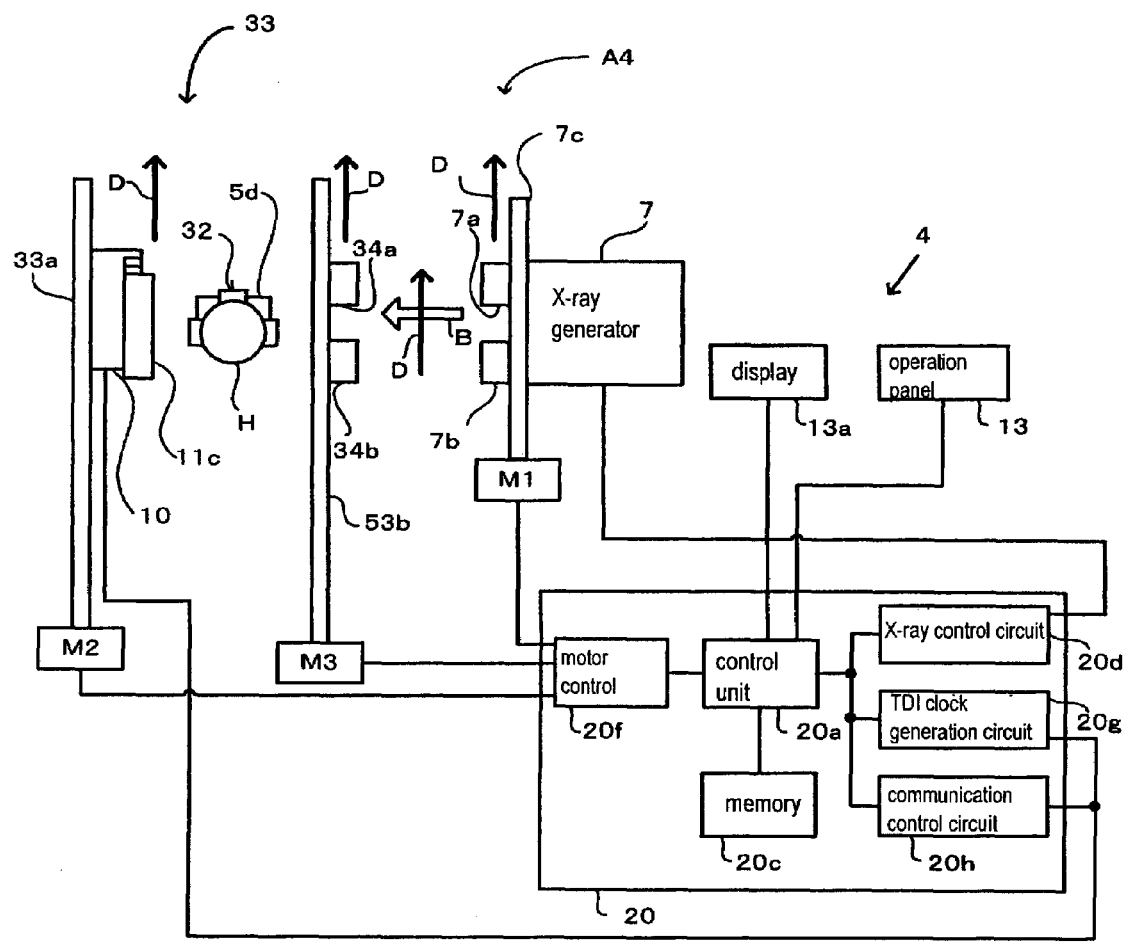
FIG. 15 is a block diagram showing the structure of a medical digital X-ray imaging apparatus capable of a linear scan radiography when the present invention is applied.

FIG. 15 is a block diagram showing the entire structure of the X-ray imaging apparatus A4. The X-ray imaging apparatus A4 is for linear scan radiography and has an X-ray generator 7, a detector 11C for radiography which receives the X-ray slit beam B generated from the X-ray generator 7 and transmitted through the object, a detector holder 10 for moving and holding the detector 11C in a detachable and speed-controllable manner, a head presser 5d (object fixing means) for fixing the object's head H to be imaged, a position detection means 32 for detecting a gradation process reference point of the object, and an apparatus body 4 for controlling the entire apparatus.

In the figure, the X-ray generator 7, the detector 11C for radiography, a support part for scanning detector, the object fixing means 5d and the position detection means 32 are shown on a flat plane when their used condition is seen from the top. The detector 11C for radiography has the same structure as the detector 11A for radiography provided for the X-ray imaging apparatus A2 in the Embodiment 2.

The X-ray generator 7 includes an X-ray tube and has a first slit member 7b made of an X-ray shielding material formed with a first slit 7a which is an opening to limit the X-ray beam widely radiated from the tube into a fixed direction and a fixed area to irradiate on a target spot, a first slit moving axis 7c for moving the first slit member 7b in the direction D shown in the figure while controlling the speed and the position, and a first slit moving motor M1 for driving the first slit moving axis 7c.

Support part 33 of detector for radiography has the detector holder 10 for detachably holding the detector 11C for radiography, a detector moving axis 33a for moving the detector holder 10 in the direction D shown in the figure so as to control the speed and the position, and a detector moving motor M2 for driving the moving axis 33a. It also has a second slit member 34b made of an X-ray shielding material which has a second slit 34a serving as an opening for passing X-rays for further limiting the X-ray slit beam B, which has been limited by the first slit 7a of the X-ray generator 7, into a fixed area before being radiated on the object's head H. It also has a second slit moving axis 33c for moving the second slit member 34b in the direction D shown in the figure so as to control the speed and the position, and a second slit moving motor M3 for driving the second slit moving axis 33c. On the other hand, the detector moving motor M2 and the second slit moving motor M3 may not be provided separately, and they may be mechanically linked by means of a timing belt so as to remove one motor.

The object's head holding means 5d (object fixing means) is constructed so as to fix the object's head H at a fixed position regardless of the movement into D direction of the detection holder 10 of the support part 33 of the detector for radiography and the second slit member 34b.

The apparatus body 4 has a control part 20 which includes a control unit 20a comprised of MPU (CPU) for achieving a central control function, a memory 20c for storing several kinds of control programs which are processed by the control unit 20a, an X-ray radiation control circuit 20d, a motor control circuit 20f, a TDI clock generation circuit 20g, and a communication control circuit 20h. The apparatus body 4 further has an operation panel 13 for receiving several operational instructions and a display means 13a for displaying X-ray images. The motor control circuit 20f is connected with the first slit moving motor M1, the detector moving motor M2, and the second slit moving motor M3 to be controlled.

According to the X-ray imaging apparatus A4, the X-ray generator 7 and the detector 11C for radiography are provided so as to interpose the object fixing means 5d as shown in the figure. When the first slit 7a, the second slit 34a and the detector 11C for radiography are synchronously moved with respect to the object's head H fixed with the head presser (head holding means) 5d, the object's head H is scanned with the X-ray slit beam B while the X-ray slit beam B radiated from the X-ray generator 7 and the detector 11C for radiography are synchronously moved into the same direction D, then the linear scan X-ray image of the object's head H is obtained. In such a case, the scanning speed (moving speed into the direction D) of X-ray slit beam B is controlled based on the stored charge signals which are the X-ray receiving data obtained by the scanning detector 11C for radiography.

When the transmitted amount is large while a hard tissue area is scanned, the radiation dosage of X-ray slit beam B which is radiated on the hard tissue area per unit time is reduced by increasing the scanning speed. On the other hand, the transmitted amount is small, the radiation dosage of X-ray slit beam B which is radiated on the hard tissue area per unit time is increased by reducing the scanning speed.

Further according to such a linear scan radiography, the detector 11C for radiography used for the X-ray imaging apparatus A4 has the same construction as the detector 11A for radiography provided for the X-ray imaging apparatus A2 explained in the Embodiment 2, so that the automatic exposure control can be done according to the method explained in the Embodiment 1.

Figure 16:
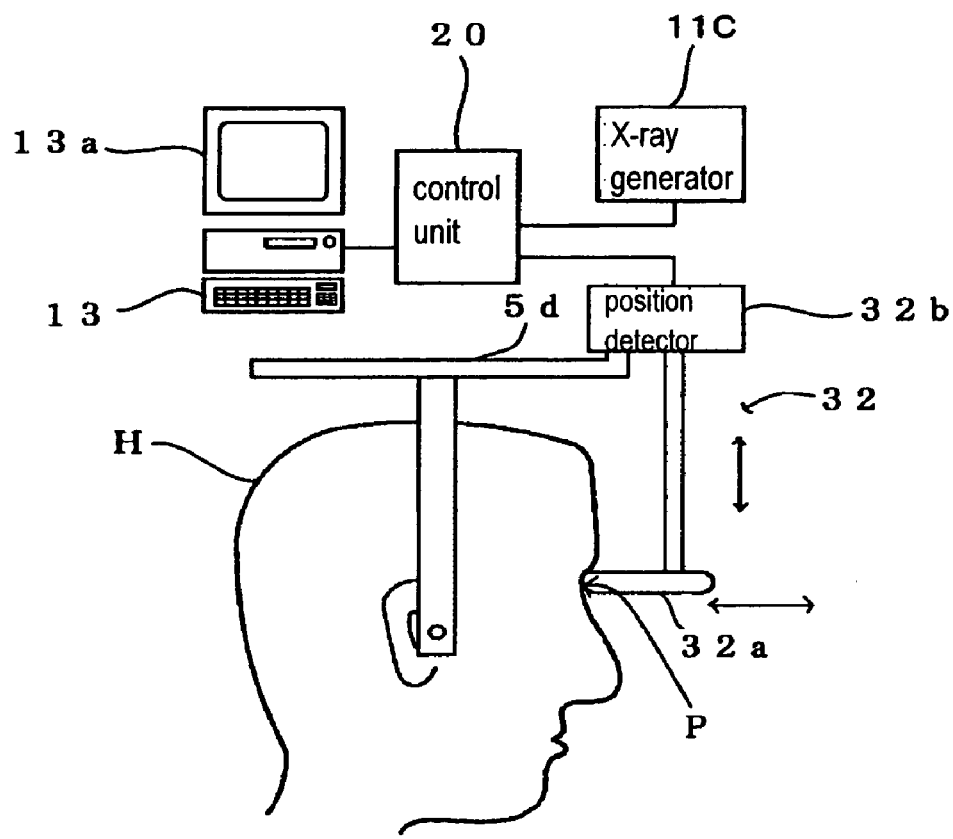
FIG. 16 shows a substantial part of a position detection means constituting the medical digital X-ray imaging apparatus of FIG. 15.

FIG. 16 is an explanatory view of the essential part of the position detection means 32 shown in FIG. 15. The position detection means 32 has a contact marker 32a and a position detector 32b which supports the contact marker 32a so as to be movable up and down and right and left shown with arrows and detects the position of the contact marker 32a which is contacted with a gradation process standard point P of the object's head H. The position detector 32b is comprised of a potentiometer fixed on the head presser 5d (object fixing means).

Such constructed position detection means 31 can easily, speedy and accurately detect the gradation process standard point P (nasion which is often used for a dental cephalometric radiography, namely a forefront of the nasofrontal suture on the median plane of human head which is important for orthodontics). Further, it is unnecessary to put a detection mark on the object. The gradation process standard point P is not limited to the position of the nasion, however, any known position may be used.

Thus obtained gradation process standard point P is used for post gradation process of a soft tissue area of a liner scan X-ray image obtained by the detector 11C for radiography or for controlling the radiation amount of X-ray slit beam B for radiography.

Further, plural sets of dark current compensation tables 3 . . . 3 may be prepared corresponding to temperature, appropriate dark current compensation table 3 may be selected depending on the temperature at the time of radiography, and the dark current may be compensated. In such a case, the fluctuation component based on the temperature of dark current component which is stored in advance is further removed when the dark current component is removed, thereby obtaining a more preferable automatic exposure control result.

EMBODIMENT 5

Now explained is an embodiment wherein the present invention is applied to a medical digital X-ray imaging apparatus capable of dental radiography.

Figure 17:
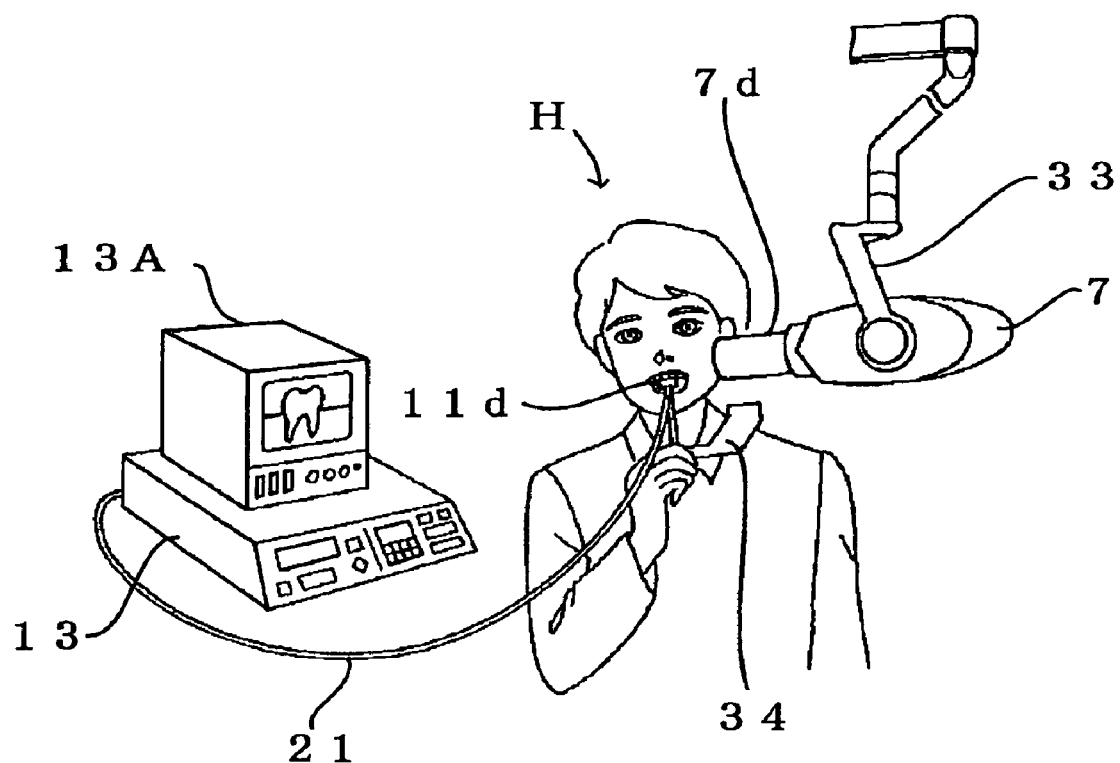
FIG. 17 shows how a medical digital X-ray imaging apparatus capable of a dental radiography is used when the present application is applied.

FIG. 17 explains how the X-ray imaging apparatus A5 is used. The object to be imaged of the X-ray imaging apparatus A5 is an intraoral area.

An X-ray generator 7 is provided so as to be able to oscillate up and down and turn horizontally with respect to a free arm 33 and the direction of an X-ray radiation tube 7d is controlled so as to irradiate X-rays into the intraoral area. A detector 11D for radiography is positioned for detecting the intensity distribution of X-rays transmitted through the intraoral area, namely for detecting the X-ray image, at a position which is opposite to the X-ray radiation tube 7d interposing the intraoral area. Namely, a positioning means 34 with the detector 11D for radiography is designed to be held by object's fingers in such a manner that the imaging plane of the detector 11D is appropriately directed into the X-ray radiating direction.

FIG. 18 is a sectional view showing the structure of the detector 11D for radiography, FIG. 18a is a horizontal section along the line A-A, and FIG. 18b is a vertical section along the line B-B.

The detector 11D for radiography is comprised of a light emitting element (scintillator) 1b for converting the radiated X-rays into a visible light, an optical fiber 1c for transmitting the emitted light from the light emitting element 1b into a light receiving surface of a solid-state image sensing device 1a, the solid-state image sensing device 1a comprised of CCD sensor for storing the electric charge generated when the fluorescence distribution transmitted by the optical fiber 1C is received and for sequentially reading out the electric charge stored for a fixed time to convert into electric signals, a board 1d made of ceramic for supporting the solid-state image sensing device 1a, and a protection case 19 for housing each structural member.

Conductive member 35 such as a thin layer of aluminum or copper is provided at the X-ray exposing face and the side of the inside of the protection case 19 so as to enclose the light emitting element 1b, the optical fiber 1c, the solid-state image sensing device 1a, and the board 1d, so that the induction noise and electrostatic serge from outside do not affect the solid-state image sensing device 1a and so on, thereby improving the anti-noise performance and the anti-serge performance. The material of conductive member 35 is preferably aluminum and beryllium with small atomic weight and the thickness is made as thin as possible like 0.01 mm to 0.1 mm, so that the X-rays entering the detector 11D for radiography do not cause attenuation and scattering.

Sealing material 19a for shielding X-rays covers at the back and side of the inside of the protection case 19 so as to prevent unnecessary scattering X-rays from entering into the back and side of the board 1d. X-ray shielding material 19b made of the sealing material 19a is provided for a part of the exposing face in the protection case 27 so as to set the dark current measuring part 1ab of the solid-state image sensing device 1a.

The board 1d has a control unit 11a (not shown) which is comprised of MPU (CPU) and has a function of image processing means 2 for dark current compensation, like the detector 11A-11C for radiography, and has a memory 11f (not shown) which previously stores the dark current compensation table 3 to which the image processing means 2 refers, like the Embodiments 2-4. Accordingly, the stored charge signals outputted from the solid-state image sensing device 1a during radiography are removed its dark current component by the image processing means 2, is stored in the memory 11f as dental X-ray images, is inputted into the operation panel 13 through a cable 21, and is displayed as an image on the display means 13A.

Next, the difference between the detector 11D for radiography used for the X-ray imaging apparatus A5 and the detectors 11A-11C for radiography used in each one of the X-ray imaging apparatus in the Embodiments 2-4.

According to the detectors 11A-11C for radiography in the Embodiments 2-4, as explained referring to FIG. 11, the picture element producing part 1aa which outputs the pixel element 1ag forming the image as the stored charge is allocated into the columns other than the lowest column of the light receiving part 1ad of the CCD sensor, the electric charge outputted from each column is subjected to time delay integration to obtain the stored charge signals of one pixel element (stored charge signals form one dimensional image). On the other hand, the detector 11D for radiography treats the electric charge from each pixel element "e" as the stored charge signals for forming a two-dimensional image.

Even when the electric charge from each pixel element "e" is treated as the stored charge signals forming a two-dimensional image, the output ratio for a fixed exposure time of the dark current measuring part and each pixel element "e" of the pixel element producing part 1aa based on the dark current component taken out of the dark current measuring part 1ab is stored in the dark current compensation table 3 in advance, and the dark current component is removed by calculation applying the output ratio stored in the dark current compensation table 3 for the stored charge signals taken from the notable pixel element 1ag during radiography to obtain the exposure control signals. Accordingly such a method is included in the present invention.

CCD sensor is used as the solid-state image sensing device 1a in this embodiment, however, MOS sensor which is constructed so as to take out the electric charge by selecting the photo diode of each pixel element by MOS transistor may be used in place of CCD sensor.

Further, plural sets of dark current compensation tables 3 . . . 3 may be prepared corresponding to temperature, an appropriate dark current compensation table 3 may be selected depending on the temperature at the time of radiography, and the dark current may be compensated. In such a case, the fluctuation component based on the temperature of dark current component which is stored in advance is further removed when the dark current component is removed, thereby obtaining a more preferable automatic exposure control result.

EMBODIMENT 6

The present invention may be used for an X-ray CT (computer tomography) imaging apparatus other than the medical digital X-ray imaging apparatus in the above-mentioned embodiments. According to the CT apparatus, a transmission radiography is executed at plural times by changing the radiation angle on the same object and thus obtained X-ray images are processed to obtain a sectional image. Therefore, the automatic exposure control of the present invention can be executed for each transmitted radiography.

The automatic exposure control method of the present invention is applied to the medical digital X-ray imaging apparatus in the above-mentioned Embodiments 2-6, however, the automatic exposure control method can be also applied to a general image producing apparatus in which a radiation light including a visible light is irradiated on the object to be examined from a radiation source to obtain an image.

The invention claimed is:

1. An automatic exposure control method for an image produced on a solid-state image sensing device in which intensity of radiation light irradiated to an object to be examined from a radiation source for producing an image is feedback controlled, wherein
the solid-state image sensing device comprises a picture element producing part where electric charges generated by way of photo-electric conversion when receiving exposure are stored as charge signals, and a dark current measuring part where a dark current is stored as charge signals without receiving exposure, and wherein
said image is produced while performing radiography in a manner that the intensity of radiation light is feedback controlled so as to keep, within a predetermined density range, the amount value which is defined by removing the charge signals stored on a specified pixel element or a specified pixel element column in said dark current measuring part of said image sensing device from the charge signals stored on a specified pixel element or a specified pixel element column in said picture element producing part of said image sensing device.

2. The automatic exposure control method for an image as set forth in claim 1, wherein
the ratio data for a fixed exposure time of the output of charge signals stored on a specified pixel element or a specified pixel element column in said dark current measuring part and in said picture element producing part, are prepared in advance, and wherein
said dark current component is removed wile performing radiography by executing a predetermined arithmetic operation for the stored charge signals taken out of said picture element producing part, based on said dark current measured in said dark current measuring part and said output ratio data.

3. The automatic exposure control method for an image as set forth in claim 1 or 2, wherein the intensity of radiation light is feedback controlled by adding predetermined delay factor for a control target value.

4. The automatic exposure control method for an image as set forth in any one of claims 1 or 2, wherein
said solid-state image sensing device executes a panoramic radiography, a cephalometric radiography, a linear scan radiography, a dental radiography or CT radiography.

5. An automatic exposure control method for an X-ray image produced on a solid-state image sensing device of a medical digital X-ray imaging apparatus in which the intensity of X-rays irradiated from an X-ray generator for radiography is feedback controlled, wherein
the solid-state image sensing device comprises a picture element producing part where electric charges generated by way of photo-electric conversion when receiving exposure are stored as charge signals, and a dark current measuring part where a dark current is stored as charge signals without receiving exposure, and wherein
said image is produced while performing radiography in a manner that the intensity of X-rays is feedback controlled so as to keep, within a predetermined density range, the amount value which is defined by removing the charge signals stored on a specified pixel element or a specified pixel element column in said dark current measuring part of said image sensing device from the charge signals stored on a specified pixel element or a specified pixel element column in said picture element producing part of said image sensing device.

6. The automatic exposure control method for an X-ray image as set forth in claim 5, wherein
the ratio data for a fixed exposure time between the inclination of the output charge signals stored on a specified pixel element or on a specified pixel element column in said dark current measuring part and the inclination of the output charge signals stored on a specified pixel element or on a specified pixel element column in said picture element producing part, are prepared in advance, and wherein
said image is produced while performing radiography in a manner that the intensity of X-rays is feedback controlled so as to keep the image to be within a predetermined density range while removing a dark current component by executing a predetermined arithmetic operation based on said dark current component taken out of said dark current measuring part and said ratio data.

7. The automatic exposure control method for an X-ray image as set forth in claim 5 or 6, wherein a feedback control of said intensity of X-rays is executed by controlling at least one of an X-ray scanning speed, an X-ray tube current and an X-ray tube voltage.

8. An automatic exposure control system of a medical digital X-ray imaging apparatus in which the intensity of X-rays irradiated from an X-ray generator for radiography is feedback controlled, said system comprising:
a solid-state image sensing device comprising a picture element producing part where electric charges generated by way of photo-electric conversion when receiving exposure are stored as charge signals, and a dark current measuring part where a dark current is stored as charge signals without receiving exposure, and
a control means for producing said image on said solid-state image sensing device by feedback controlling the intensity of X-rays while performing radiography, so as to keep, within a predetermined range, the amount value which is defined by removing the charge signals stored on a specified pixel element or a specified pixel element column in said dark current measuring part of said image sensing device from the charge signals stored on a specified pixel element or a specified pixel element column in said picture element producing part of said image sensing device.

9. The automatic exposure control system as set forth in claim 8, said system comprising:
a memory for storing in advance the ratio data for a fixed exposure time between the inclination of the change in the output charge signals stored on a specified pixel element or on a specified pixel element column in said dark current measuring part and the inclination of the change in the output charge signals stored on a specified pixel element or on a specified pixel element column in said picture element producing part; and a control means for feedback controlling the intensity of X-rays so as to keep the image to be within a predetermined density range while removing a dark current component by executing a predetermined arithmetic operation based on said dark current component taken out of said dark current measuring part and said ratio data.

10. The automatic exposure control method as set forth in claim 8 or 9, wherein a feedback control of said intensity of X-rays is executed by controlling at least one of an X-ray scanning speed, an X-ray tube current, an X-ray tube voltage, and a gradation process.

* * * * *